United States Patent
Prakash et al.

(10) Patent No.: US 8,035,570 B2
(45) Date of Patent: Oct. 11, 2011

(54) HIGH-STRENGTH MICROWAVE ANTENNA ASSEMBLIES

(75) Inventors: Mani N. Prakash, Boulder, CO (US); Francesca Rossetto, Longmont, CO (US); Anthony C. Lee, San Francisco, CA (US); Steven Kim, Los Altos, CA (US); Ted Su, Sunnyvale, CA (US); Jonathan L. Glassman, Cambridge, MA (US)

(73) Assignee: Vivant Medical, Inc., Boulder, CO (US)

( * ) Notice: Subject to any disclaimer, the term of this patent is extended or adjusted under 35 U.S.C. 154(b) by 366 days.

(21) Appl. No.: 12/419,395

(22) Filed: Apr. 7, 2009

(65) Prior Publication Data

US 2010/0082082 A1 Apr. 1, 2010

Related U.S. Application Data

(63) Continuation of application No. 11/493,392, filed on Jul. 26, 2006, now Pat. No. 7,527,623, which is a continuation of application No. 10/961,994, filed on Oct. 7, 2004, now Pat. No. 7,147,632, which is a continuation of application No. 10/052,848, filed on Nov. 2, 2001, now Pat. No. 6,878,147.

(51) Int. Cl.
  *H01Q 9/04* (2006.01)
(52) U.S. Cl. ............. 343/790; 606/33; 606/41; 607/101
(58) Field of Classification Search ............. 343/790, 343/791, 792; 606/33, 41; 607/101, 102
See application file for complete search history.

(56) References Cited

U.S. PATENT DOCUMENTS

| | | | |
|---|---|---|---|
| 3,750,181 A * | 7/1973 | Kuecken | 343/790 |
| 4,140,130 A | 2/1979 | Storm, III | |
| 4,292,960 A | 10/1981 | Paglione | |
| 4,311,154 A | 1/1982 | Sterzer et al. | |
| 4,397,313 A | 8/1983 | Vaguine | |
| 4,557,272 A | 12/1985 | Carr | |
| 4,583,589 A | 4/1986 | Kasevich | |

(Continued)

FOREIGN PATENT DOCUMENTS

EP 0 667 126 8/1995

(Continued)

OTHER PUBLICATIONS

Int'l Search Report from corresponding European Application No. EP 02 78 6604 mailed Feb. 10, 2010.

(Continued)

*Primary Examiner* — David G Phan

(57) ABSTRACT

Various high-strength microwave antenna assemblies are described herein. The microwave antenna has a radiating portion connected by a feedline to a power generating source, e.g., a generator. The antenna is a dipole antenna with the distal end of the radiating portion being tapered and terminating at a tip to allow for direct insertion into tissue. Antenna rigidity comes from placing distal and proximal radiating portions in a pre-stressed state, assembling them via threaded or overlapping joints, or fixedly attaching an inner conductor to the distal portion. The inner conductor is affixed to the distal portion by, e.g., welding, brazing, soldering, or by adhesives. A junction member made from a hard dielectric material, e.g., ceramic, can be placed between the two portions and can have uniform or non-uniform shapes to accommodate varying antenna designs. Electrical chokes may also be used to contain returning currents to the distal end of the antenna.

8 Claims, 18 Drawing Sheets

U.S. PATENT DOCUMENTS

| | | |
|---|---|---|
| 4,612,940 A | 9/1986 | Kasevich et al. |
| 4,621,642 A | 11/1986 | Chen |
| 4,658,836 A | 4/1987 | Turner |
| 4,669,475 A | 6/1987 | Turner |
| 4,700,716 A | 10/1987 | Kasevich et al. |
| 4,776,086 A | 10/1988 | Kasevich et al. |
| 4,800,899 A | 1/1989 | Elliott |
| 5,190,054 A | 3/1993 | Fetter et al. |
| 5,221,269 A | 6/1993 | Miller et al. |
| 5,246,438 A | 9/1993 | Langberg |
| 5,249,585 A | 10/1993 | Turner et al. |
| 5,275,597 A | 1/1994 | Higgins et al. |
| 5,281,217 A | 1/1994 | Edwards et al. |
| 5,301,687 A | 4/1994 | Wong et al. |
| 5,314,466 A | 5/1994 | Stern et al. |
| 5,344,441 A | 9/1994 | Gronauer |
| 5,370,644 A | 12/1994 | Langberg |
| 5,405,346 A | 4/1995 | Grundy et al. |
| 5,500,012 A | 3/1996 | Brucker et al. |
| 5,507,743 A | 4/1996 | Edwards et al. |
| 5,520,684 A | 5/1996 | Imran |
| 5,536,267 A | 7/1996 | Edwards et al. |
| 5,556,377 A | 9/1996 | Rosen et al. |
| 5,599,294 A | 2/1997 | Edwards et al. |
| 5,720,718 A | 2/1998 | Rosen et al. |
| 5,776,176 A | 7/1998 | Rudie |
| 5,800,486 A | 9/1998 | Thome et al. |
| 5,810,804 A | 9/1998 | Gough et al. |
| 5,829,519 A | 11/1998 | Uthe |
| 5,871,523 A | 2/1999 | Fleischman et al. |
| 5,897,554 A | 4/1999 | Chia et al. |
| 5,902,251 A | 5/1999 | vanHooydonk |
| 5,904,691 A | 5/1999 | Barnett et al. |
| 5,904,709 A | 5/1999 | Arndt et al. |
| 5,938,692 A | 8/1999 | Rudie |
| 5,944,749 A | 8/1999 | Fenn |
| 5,951,547 A | 9/1999 | Gough et al. |
| 5,957,969 A | 9/1999 | Warner et al. |
| 5,964,755 A | 10/1999 | Edwards |
| 5,974,343 A | 10/1999 | Brevard et al. |
| 5,980,563 A | 11/1999 | Tu et al. |
| 6,016,811 A | 1/2000 | Knopp et al. |
| 6,024,743 A | 2/2000 | Edwards |
| 6,026,331 A | 2/2000 | Feldberg et al. |
| 6,032,078 A | 2/2000 | Rudie |
| 6,056,744 A | 5/2000 | Edwards |
| 6,059,780 A | 5/2000 | Gough et al. |
| 6,073,051 A | 6/2000 | Sharkey et al. |
| 6,080,150 A | 6/2000 | Gough et al. |
| 6,097,985 A | 8/2000 | Kasevich et al. |
| 6,106,518 A | 8/2000 | Wittenberger et al. |
| 6,122,551 A | 9/2000 | Rudie et al. |
| 6,134,476 A | 10/2000 | Arndt et al. |
| 6,146,379 A | 11/2000 | Fleischman et al. |
| 6,176,856 B1 | 1/2001 | Jandak et al. |
| 6,181,970 B1 | 1/2001 | Kasevich |
| 6,217,528 B1 | 4/2001 | Koblish et al. |
| 6,223,086 B1 | 4/2001 | Carl et al. |
| 6,233,490 B1 | 5/2001 | Kasevich |
| 6,245,064 B1 | 6/2001 | Lesh et al. |
| 6,251,128 B1 | 6/2001 | Knopp et al. |
| 6,275,738 B1 | 8/2001 | Kasevich et al. |
| 6,277,113 B1 | 8/2001 | Berube |
| 6,290,715 B1 | 9/2001 | Sharkey et al. |
| 6,306,132 B1 | 10/2001 | Moorman et al. |
| 6,325,796 B1 | 12/2001 | Berube et al. |
| 6,330,479 B1 | 12/2001 | Stauffer |
| 6,346,104 B2 | 2/2002 | Daly et al. |
| 6,347,251 B1 | 2/2002 | Deng |
| 6,350,262 B1 | 2/2002 | Ashley |
| 6,355,033 B1 | 3/2002 | Moorman et al. |
| 6,377,225 B1 * | 4/2002 | Silverstein .................... 343/790 |
| 6,405,733 B1 | 6/2002 | Fogarty et al. |
| 6,471,696 B1 | 10/2002 | Berube et al. |
| 6,496,737 B2 | 12/2002 | Rudie et al. |
| 6,496,738 B2 | 12/2002 | Carr |
| 6,506,189 B1 | 1/2003 | Rittman et al. |
| 6,514,251 B1 | 2/2003 | Ni et al. |
| 6,530,922 B2 | 3/2003 | Cosman et al. |
| 6,564,806 B1 | 5/2003 | Fogarty et al. |
| 6,569,159 B1 | 5/2003 | Edwards et al. |
| 6,663,624 B2 | 12/2003 | Edwards et al. |
| 6,685,700 B2 | 2/2004 | Behl et al. |
| 6,699,241 B2 | 3/2004 | Rappaport et al. |
| 6,722,371 B1 | 4/2004 | Fogarty et al. |
| 6,752,154 B2 | 6/2004 | Fogarty et al. |
| 6,752,767 B2 | 6/2004 | Turovskiy et al. |
| 6,836,256 B2 * | 12/2004 | Hung ........................... 343/790 |
| 6,878,147 B2 | 4/2005 | Prakash et al. |
| 6,898,454 B2 * | 5/2005 | Atalar et al. .................. 600/410 |
| 6,957,108 B2 * | 10/2005 | Turner et al. .................. 607/101 |
| 7,128,739 B2 | 10/2006 | Prakash et al. |
| 7,147,632 B2 | 12/2006 | Prakash et al. |
| 7,174,217 B2 | 2/2007 | Rioux et al. |
| 7,190,989 B1 | 3/2007 | Swanson et al. |
| 7,207,985 B2 | 4/2007 | Duong et al. |
| 7,217,282 B2 | 5/2007 | Ginsburg et al. |
| 7,229,437 B2 | 6/2007 | Johnson et al. |
| 7,231,259 B2 | 6/2007 | Jenney et al. |
| 7,234,225 B2 | 6/2007 | Johnson et al. |
| 7,234,977 B2 | 6/2007 | Westlund et al. |
| 7,235,070 B2 | 6/2007 | Vanney |
| 7,238,166 B2 | 7/2007 | Callister |
| 7,238,184 B2 | 7/2007 | Megerman et al. |
| 7,238,194 B2 | 7/2007 | Monstadt et al. |
| 7,241,293 B2 | 7/2007 | Davison |
| 7,244,254 B2 | 7/2007 | Brace et al. |
| 7,245,955 B2 | 7/2007 | Rashidi |
| 7,264,619 B2 | 9/2007 | Venturelli |
| 7,270,656 B2 | 9/2007 | Gowda et al. |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,270,662 B2 | 9/2007 | Visram et al. |
| 7,271,363 B2 | 9/2007 | Lee et al. |
| 7,273,480 B2 | 9/2007 | Young et al. |
| 7,276,061 B2 | 10/2007 | Schaer et al. |
| 7,282,049 B2 | 10/2007 | Orszulak et al. |
| 7,285,116 B2 | 10/2007 | de la Rama |
| 7,293,562 B2 | 11/2007 | Malecki et al. |
| 7,300,438 B2 | 11/2007 | Falwell et al. |
| 7,301,131 B2 | 11/2007 | Gauthier et al. |
| 7,306,592 B2 | 12/2007 | Morgan et al. |
| 7,309,325 B2 | 12/2007 | Mulier et al. |
| 7,309,336 B2 | 12/2007 | Ashley et al. |
| 7,311,702 B2 | 12/2007 | Tallarida et al. |
| 7,311,703 B2 | 12/2007 | Turovskiy et al. |
| 7,311,705 B2 | 12/2007 | Sra |
| 7,317,949 B2 | 1/2008 | Morrison et al. |
| 7,318,822 B2 | 1/2008 | Darmos et al. |
| 7,318,823 B2 | 1/2008 | Sharps et al. |
| 7,318,824 B2 | 1/2008 | Prakash et al. |
| 7,319,904 B2 | 1/2008 | Cross, Jr. et al. |
| 7,326,204 B2 | 2/2008 | Paul et al. |
| 7,326,205 B2 | 2/2008 | Paul et al. |
| 7,326,206 B2 | 2/2008 | Paul et al. |
| 7,331,957 B2 | 2/2008 | Woloszko et al. |
| 7,337,009 B2 | 2/2008 | Schell |
| 2001/0001819 A1 | 5/2001 | Lee et al. |
| 2001/0037812 A1 | 11/2001 | Dobak, III et al. |
| 2002/0022832 A1 | 2/2002 | Mikus et al. |
| 2002/0087151 A1 | 7/2002 | Mody et al. |
| 2002/0133148 A1 | 9/2002 | Daniel et al. |
| 2002/0147444 A1 | 10/2002 | Shah et al. |
| 2002/0198520 A1 | 12/2002 | Coen et al. |
| 2003/0004506 A1 | 1/2003 | Messing |
| 2003/0065317 A1 | 4/2003 | Rudie et al. |
| 2003/0069578 A1 | 4/2003 | Hall et al. |
| 2003/0109862 A1 | 6/2003 | Prakash et al. |
| 2003/0195499 A1 | 10/2003 | Prakash et al. |
| 2004/0168692 A1 | 9/2004 | Fogarty et al. |
| 2004/0267156 A1 | 12/2004 | Turovskiy et al. |
| 2005/0015081 A1 | 1/2005 | Turovskiy et al. |
| 2005/0085881 A1 | 4/2005 | Prakash et al. |
| 2006/0259024 A1 | 11/2006 | Turovskiy et al. |
| 2006/0264923 A1 | 11/2006 | Prakash et al. |
| 2006/0282069 A1 | 12/2006 | Prakash et al. |

| | | | |
|---|---|---|---|
| 2007/0027451 A1 | 2/2007 | Desinger et al. | |
| 2007/0073282 A1 | 3/2007 | McGaffigan et al. | |
| 2007/0123765 A1 | 5/2007 | Hetket et al. | |
| 2007/0129715 A1 | 6/2007 | Eggers et al. | |
| 2007/0135879 A1 | 6/2007 | McIntyre et al. | |
| 2007/0142829 A1 | 6/2007 | Ahn et al. | |
| 2007/0149964 A1 | 6/2007 | Kawabata et al. | |
| 2007/0156048 A1 | 7/2007 | Panescu et al. | |
| 2007/0156128 A1 | 7/2007 | Jimenez | |
| 2007/0156132 A1 | 7/2007 | Drysen | |
| 2007/0156133 A1 | 7/2007 | McDaniel et al. | |
| 2007/0173680 A1 | 7/2007 | Rioux et al. | |
| 2007/0173798 A1 | 7/2007 | Adams et al. | |
| 2007/0173812 A1 | 7/2007 | Bonan et al. | |
| 2007/0179375 A1 | 8/2007 | Fuimaono et al. | |
| 2007/0179497 A1 | 8/2007 | Eggers et al. | |
| 2007/0185478 A1 | 8/2007 | Cosentino | |
| 2007/0191825 A1 | 8/2007 | Cronin et al. | |
| 2007/0203551 A1 | 8/2007 | Cronin et al. | |
| 2007/0208334 A1 | 9/2007 | Woloszko et al. | |
| 2007/0208335 A1 | 9/2007 | Woloszko et al. | |
| 2007/0208383 A1 | 9/2007 | Williams | |
| 2007/0213700 A1 | 9/2007 | Davison et al. | |
| 2007/0213703 A1 | 9/2007 | Naam et al. | |
| 2007/0215163 A1 | 9/2007 | Harrington et al. | |
| 2007/0219551 A1 | 9/2007 | Honour et al. | |
| 2007/0225701 A1 | 9/2007 | O'Sullivan | |
| 2007/0233057 A1 | 10/2007 | Konishi | |
| 2007/0244529 A1 | 10/2007 | Choi et al. | |
| 2007/0250053 A1 | 10/2007 | Fernald et al. | |
| 2007/0250054 A1 | 10/2007 | Drake | |
| 2007/0250055 A1 | 10/2007 | Johnson et al. | |
| 2007/0250056 A1 | 10/2007 | Vanney | |
| 2007/0255276 A1 | 11/2007 | Sliwa, Jr. et al. | |
| 2007/0260235 A1 | 11/2007 | Podhajsky | |
| 2007/0260237 A1 | 11/2007 | Sutton et al. | |
| 2007/0270679 A1 | 11/2007 | Nguyen et al. | |
| 2007/0270791 A1 | 11/2007 | Wang et al. | |
| 2007/0276361 A1 | 11/2007 | Stevens-Wright et al. | |
| 2007/0276362 A1 | 11/2007 | Rioux et al. | |
| 2007/0282323 A1 | 12/2007 | Woloszko et al. | |
| 2007/0282324 A1 | 12/2007 | Vaska et al. | |
| 2007/0282325 A1 | 12/2007 | Young et al. | |
| 2007/0287995 A1 | 12/2007 | Mayse | |
| 2007/0287998 A1 | 12/2007 | Sharareh et al. | |
| 2007/0293853 A1 | 12/2007 | Truckai et al. | |
| 2007/0293854 A1 | 12/2007 | Pless et al. | |
| 2007/0293855 A1 | 12/2007 | Sliwa, Jr. et al. | |
| 2007/0299488 A1 | 12/2007 | Carr | |
| 2008/0004614 A1 | 1/2008 | Burdette et al. | |
| 2008/0004618 A1 | 1/2008 | Johnson et al. | |
| 2010/0114086 A1* | 5/2010 | Deem et al. | 606/33 |

FOREIGN PATENT DOCUMENTS

| | | |
|---|---|---|
| WO | WO 93/20767 | 10/1993 |
| WO | WO 93/20768 A1 | 10/1993 |
| WO | WO9518575 | 7/1995 |
| WO | WO 96/34571 | 11/1996 |
| WO | WO 97/48449 | 12/1997 |
| WO | WO 97/48450 | 12/1997 |
| WO | WO 97/48451 | 12/1997 |
| WO | WO 98/44968 | 10/1998 |
| WO | WO 99/56642 | 11/1999 |
| WO | WO 99/56643 | 11/1999 |
| WO | WO 99/56812 | 11/1999 |
| WO | WO 00/49957 | 8/2000 |
| WO | WO 00/57811 | 10/2000 |
| WO | WO 01/60235 | 8/2001 |
| WO | WO0174252 | 10/2001 |
| WO | WO 03/034932 | 5/2003 |
| WO | WO 03/039385 | 5/2003 |
| WO | WO 03/088806 | 10/2003 |
| WO | WO 03/088858 | 10/2003 |
| WO | WO 2005/011049 | 2/2005 |

OTHER PUBLICATIONS

International EP Search report EP10004951 dated Jul. 2, 2010.
International EP Search report EP 10004950 dated Jul. 2, 2010.
I Chou, C.K. (1995). "Radiofrequency Hyperthermia in Cancer Therapy," Biologic Effects of Nonionizing Electromagnetic Fields. Chapter 94, CRC Press, Inc. pp. 1424-1428.
Urologix, Inc.-Medical Professionals: Targis3 Technology http://www.urologix.com/medical/technology.html (total pgs. 3) (date prior to the filing date of the present application).

* cited by examiner

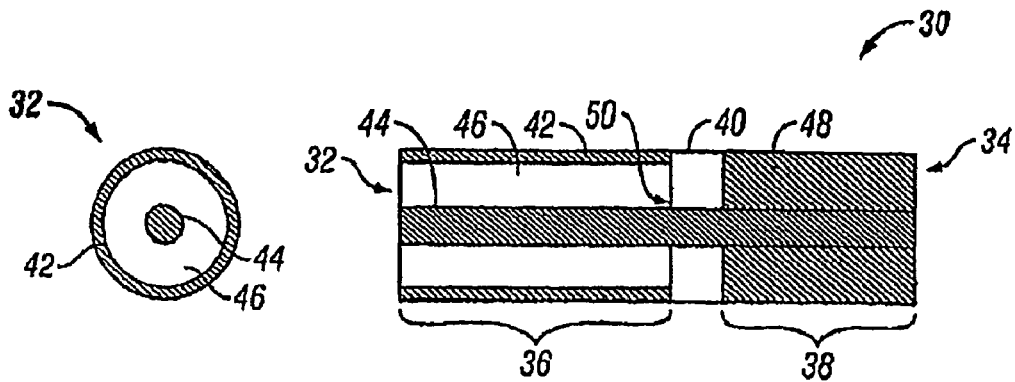
FIG. 2A
(Prior Art)
FIG. 2B
(Prior Art)
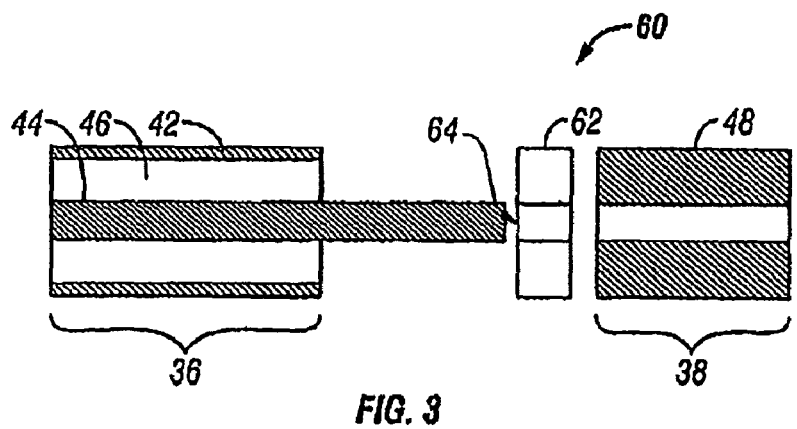
FIG. 3
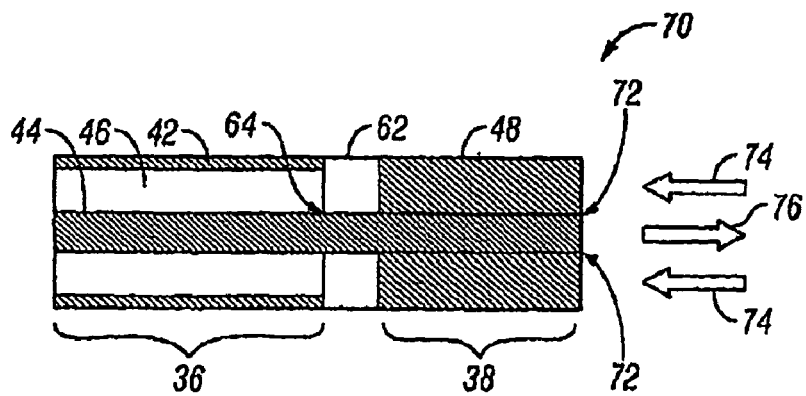
FIG. 4

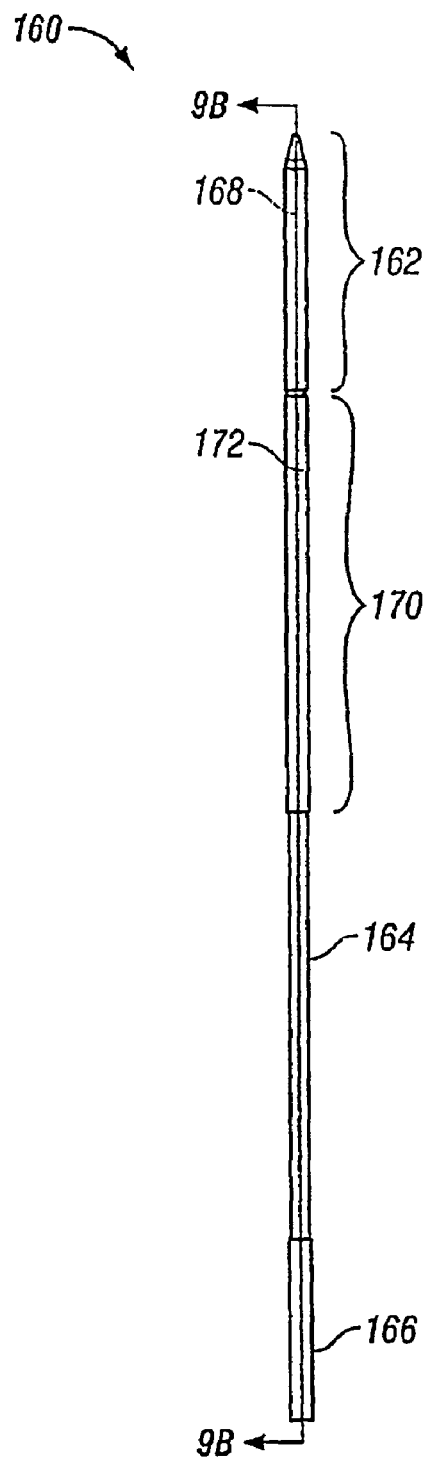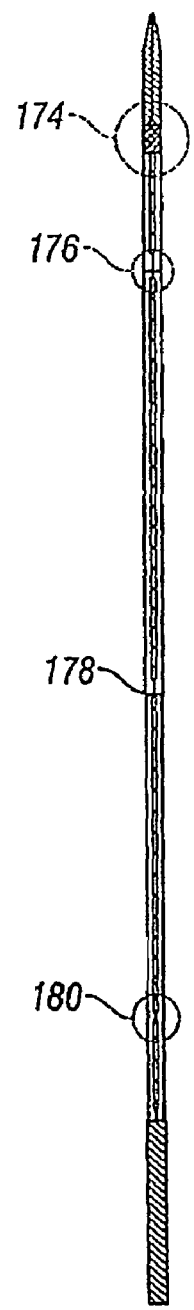
FIG. 9A                    FIG. 9B

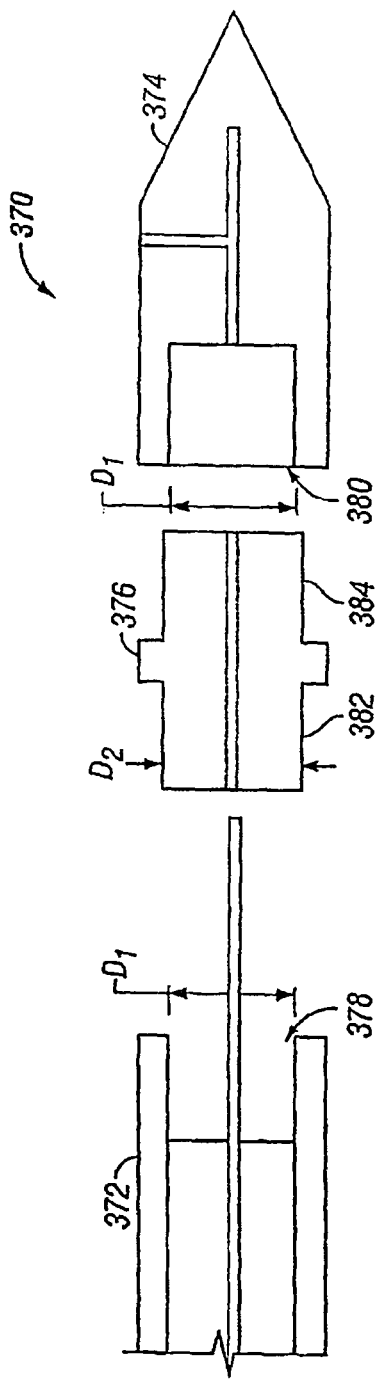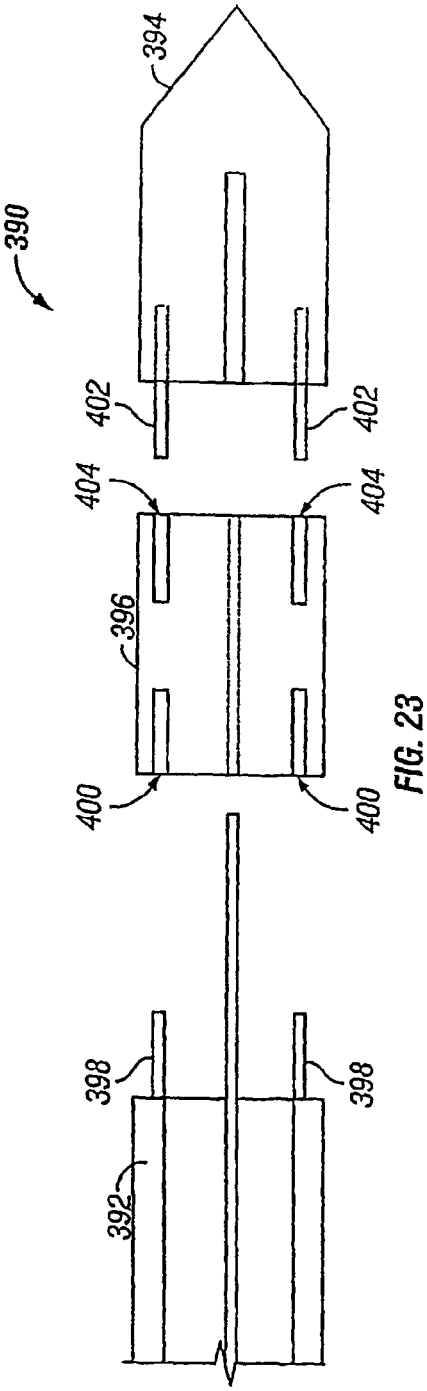

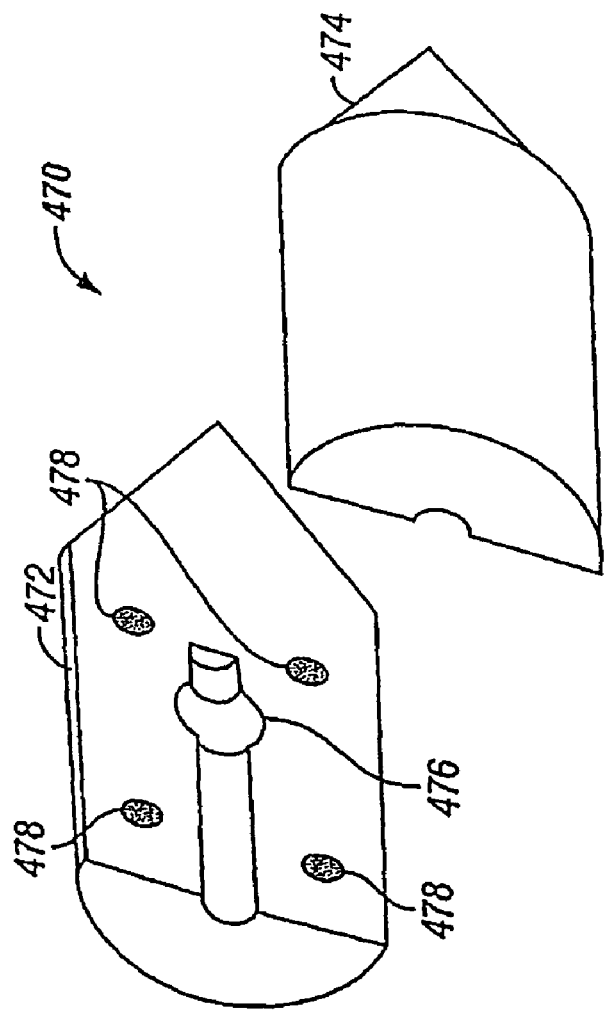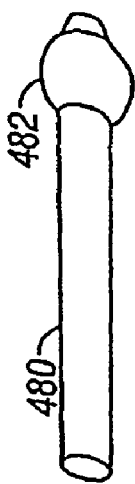
FIG. 27

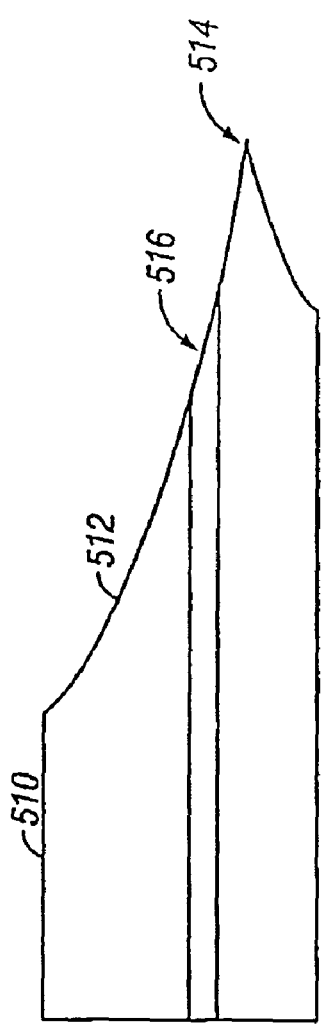
FIG. 29

HIGH-STRENGTH MICROWAVE ANTENNA ASSEMBLIES

CROSS-REFERENCE TO RELATED APPLICATIONS

This application is a continuation of U.S. application Ser. No. 11/493,392, filed Jul. 26, 2006, now U.S. Pat. No. 7,527,623 which is a continuation of U.S. application Ser. No. 10/961,994, filed Oct. 7, 2004, now U.S. Pat. No. 7,147,632, which is a continuation of U.S. application Ser. No. 10/052,848, filed Nov. 2, 2001, now U.S. Pat. No. 6,878,147, the contents of which are each hereby incorporated by reference into the present disclosure.

TECHNICAL FIELD OF THE INVENTION

The invention relates generally to microwave antenna probes which may be used in tissue ablation applications. More particularly, the invention relates to microwave antennas which may be inserted directly into tissue for diagnosis and treatment of diseases.

BACKGROUND OF THE INVENTION

In the treatment of diseases such as cancer, certain types of cancer cells have been found to denature at elevated temperatures which are slightly lower than temperatures normally injurious to healthy cells. These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and, organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control. This is partly why a more direct and precise method of applying microwave radiation has been sought.

Presently, there are several types of microwave probes in use, e.g., monopole, dipole, and helical. One type is a monopole antenna probe, which consists of a single, elongated microwave conductor exposed at the end of the probe. The probe is sometimes surrounded by a dielectric sleeve. The second type of microwave probe commonly used is a dipole antenna, which consists of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

The typical microwave antenna has a long, thin inner conductor which extends along the axis of the probe and is surrounded by a dielectric material and is further surrounded by an outer conductor around the dielectric material such that the outer conductor also extends along the axis of the probe. In another variation of the probe which provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or a combination thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growths of cells. However, at slightly elevated temperatures above the approximate range of 43° C. to 45° C., thermal damage to most types of normal cells is routinely observed; accordingly, great care must be taken not to exceed these temperatures in healthy tissue.

However, many types of malignancies are difficult to reach and treat using non-invasive techniques or by using invasive antenna probes designed to be inserted into a normal body orifice, i.e., a body opening which is easily accessible. These types of conventional probes may be more flexible and may also avoid the need to separately sterilize the probe; however, they are structurally weak and typically require the use of an introducer or catheter to gain access to within the body. Moreover, the addition of introducers and catheters necessarily increase the diameter of the incision or access opening into the body thereby making the use of such probes more invasive and further increasing the probability of any complications that may arise.

Structurally stronger invasive probes exist and are typically long, narrow, needle-like antenna probes which may be inserted directly into the body tissue to directly access a site of a tumor or other malignancy. Such rigid probes generally have small diameters which aid not only in ease of use but also reduce the resulting trauma to the patient. A convenience of rigid antenna probes capable of direct insertion into tissue is that the probes may also allow for alternate additional uses given different situations. However, such rigid, needle-like probes commonly experience difficulties in failing to provide uniform patterns of radiated energy; they fail to provide uniform heating axially along and radially around an effective length of the probe; and it is difficult to otherwise control and direct the heating pattern when using such probes.

Accordingly, there remains a need for a microwave antenna probe which overcomes the problems discussed above. There also exists a need for a microwave antenna probe which is structurally robust enough for direct insertion into tissue without the need for additional introducers or catheters and which produces a controllable and predictable heating pattern.

SUMMARY OF THE INVENTION

A microwave antenna assembly which is structurally robust enough for unaided direct insertion into tissue is described herein. The microwave antenna assembly is generally comprised of a radiating portion which may be connected to a feedline (or shaft) which in turn may be connected by a cable to a power generating source such as a generator. The microwave assembly may be a monopole microwave antenna assembly but is preferably a dipole assembly. The distal portion of the radiating portion preferably has a tapered end which terminates at a tip to allow for the direct insertion into tissue with minimal resistance. The proximal portion is located proximally of the distal portion, and a junction member is preferably located between both portions.

The adequate rigidity necessary for unaided direct insertion of the antenna assembly into tissue, e.g., percutaneously, preferably comes in part by a variety of different methods. Some of the methods include assembling the antenna under a pre-stressed condition prior to insertion into tissue. This may be accomplished in part by forcing an inner conductor, which runs longitudinally through the assembly, into a tensile condition by preferably affixing the inner conductor distal end to the distal radiating portion of the antenna assembly. Another method includes configuring the proximal and distal radiating portions of the antenna to mechanically fasten to each other. That is, the proximal and distal radiating portions may be configured to "screw" into one another directly or to a junction member located between the two portions and which is threaded such that the portions each screw onto the junction member separately.

Another method includes attaching the proximal and distal radiating portions together by creating overlapping or interfitting joints. In this variation, either the proximal or the distal radiating portion may be configured to create an overlapping joint by interfitting with each other through a variety of joints. For instance, the distal portion may be configured to intimately fit within a receiving cavity or channel at the distal end of the proximal portion. The two portions may also be configured to have a number of pins or conical members extending to join the two. Alternatively, the two portions may be frictionally interfitted by an interference fitted joint; or depressible/retractable projections may be disposed on either portion to interfit with corresponding depressions in the opposite portion.

To further aid in strengthening the antenna assemblies, a variety of methods may also be used for attaching the tip or distal portion. For instance, a variation may have a distal portion which may screw onto a threaded inner conductor or another variation may have an inner conductor having an anchoring element capable of holding the inner conductor within a splittable distal portion. Furthermore, a multi-sectioned distal portion may also be utilized for first attaching an inner conductor to the distal portion and then assembling the distal portion with additional variable sections. In many of the variations described herein, it may be preferable to have a dielectric material applied as a layer or coating between the two radiating portions.

Affixing the inner conductor within the distal radiating portion may be accomplished in a variety of ways, for instance, welding, brazing, soldering, or through the use of adhesives. Forcing the inner conductor into a tensile condition helps to force the outer diameter of the antenna into a compressive state. This bi-directional stress state in turn aids in rigidizing the antenna assembly.

To enable a compressive state to exist near the outer diameter, the junction member between the distal and the proximal radiating portions in some of the variations is preferably made from a sufficiently hard dielectric material, e.g., ceramic materials. The hardness of the junction member aids in transferring the compressive forces through the antenna assembly without buckling or kinking during antenna insertion into tissue. Furthermore, materials such as ceramic generally have mechanical properties where fracturing or cracking in the material is more likely to occur under tensile loading conditions. Accordingly, placing a junction under pre-stressed conditions, particularly a junction made of ceramic, may aid in preventing mechanical failure of the junction if the antenna were to incur bending moments during insertion into tissue which could subject portions of the junction under tensile loads. The junction member may also be made into uniform or non-uniform, e.g., stepped, shapes to accommodate varying antenna assembly designs.

Moreover, to improve the energy focus of an antenna assembly, an electrical choke may also be used in any of the variations described herein to contain returning currents to the distal end of the antenna assembly. Generally, the choke may be disposed on top of a dielectric material on the antenna proximally of the radiating section. The choke is preferably comprised of a conductive layer and may be further covered by a tubing or coating to force the conductive layer to conform to the underlying antenna.

Additionally, variations on the choke, the tubing or coating, any sealant layers, as well as other layers which may be disposed over the antenna assembly may be used. Certain layers, e.g., a heatshrink layer disposed over the antenna assembly, may have wires or strands integrated within the layer to further strengthen the antenna assembly. Kevlar wires, for instances, may be integrally formed into the layer and oriented longitudinally with the antenna axis to provide additional strength.

BRIEF DESCRIPTION OF THE DRAWINGS

FIGS. 2A and 2B show an end view and a cross-sectional view, respectively, of a conventional dipole microwave antenna assembly.

FIG. 3 shows an exploded cross-sectional view of a variation on a pre-stressed antenna assembly.

FIG. 4 shows the assembled pre-stressed antenna assembly of FIG. 3 and the directions of stress loads created within the assembly.

FIG. 9A shows a side view of another variation on a pre-stressed antenna assembly having an electrical choke.

FIG. 9B shows a cross-sectional view of the assembly of FIG. 9A.

FIG. 22 shows an exploded cross-sectional side view of another variation where the antenna may be assembled using overlapping interference-fitted joints.

FIG. 23 shows another variation in an exploded cross-sectional side view of an antenna assembled via a junction member and multiple pins.

FIG. 27 shows an isometric exploded view of another variation on attaching the distal portion by anchoring the inner conductor within a splittable distal portion.

FIG. 29 shows a cross-sectioned side view of an alternative distal portion having an arcuate or curved sloping face to facilitate antenna assembly as well as entry into tissue.

DETAILED DESCRIPTION OF THE INVENTION

Figure 1:
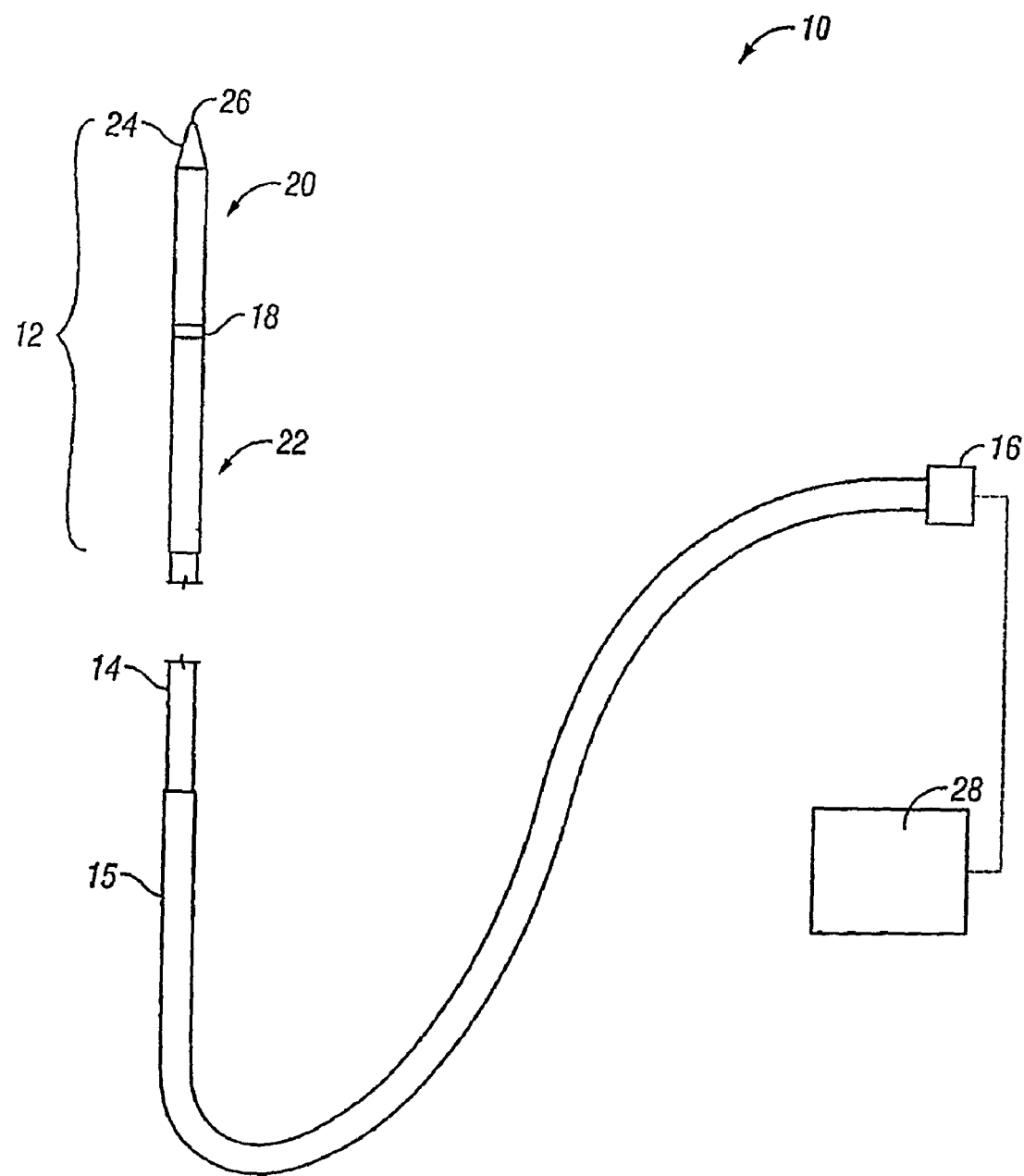
FIG. 1 shows a representative diagram of a variation of a microwave antenna assembly.

In invasively treating diseased areas of tissue in a patient, trauma may be caused to the patient resulting in pain and other complications. Various microwave antenna assemblies, as described herein, are less traumatic than devices currently available and as described in further detail below, methods of manufacturing such devices are also described. Generally, an apparatus of the present invention allows for the direct insertion of a microwave antenna into tissue for the purposes of diagnosis and treatment of disease. FIG. 1 shows a representative diagram of a variation of a microwave antenna assembly 10 of the present invention. The antenna assembly 10 is generally comprised of radiating portion 12 which may be connected by feedline 14 (or shaft) via cable 15 to connector 16, which may further connect the assembly 10 to a power generating source 28, e.g., a generator. Assembly 10, as shown, is a dipole microwave antenna assembly, but other antenna assemblies, e.g., monopole or leaky wave antenna assemblies, may also utilize the principles set forth herein. Distal portion 20 of radiating portion 12 preferably has a tapered end 24 which terminates at a tip 26 to allow for insertion into tissue with minimal resistance. In those cases where the radiating portion 12 is inserted into a pre-existing opening, tip 26 may be rounded or flat.

In some applications a microwave antenna requires adequate structural strength to prevent bending of the antenna, e.g., where the antenna is directly inserted into tissue, where the antenna undergoes bending moments after insertion, etc. Accordingly, there are various configurations to increase the antenna strength without compromising desirable radiative properties and the manufacturability of such an antenna. One configuration involves placing the antenna assembly under a compressive load to stiffen the radiating portions. Another configuration involves mechanically fastening, e.g., in a screw-like manner, the radiating portions together to provide a joint which will withstand bending moments. A further configuration may also involve creating overlapping joints between the radiating portions of the antenna assembly to provide a high-strength antenna. Furthermore, alternate configurations of attaching a distal tip or distal radiating portion to an antenna may be utilized to further increase the antenna strength.

Antenna Assembly Via Compression

Generally, the antenna assembly 10 in FIG. 1 shows a variation where a compressive load may be used to increase antenna strength. Proximal portion 22 is located proximally of distal portion 20, and junction member 18 is preferably located between both portions such that a compressive force is applied by distal and proximal portions 20, 22 upon junction member 18. Placing distal and proximal portions 20, 22 in a pre-stressed condition prior to insertion into tissue enables assembly 10 to maintain a stiffness that is sufficient to allow for unaided insertion into the tissue while maintaining a minimal antenna diameter, as described in detail below.

Feedline 14 may electrically connect antenna assembly 10 via cable 15 to generator 28 and usually comprises a coaxial cable made of a conductive metal which may be semi-rigid or flexible. Feedline 14 may also have a variable length from a proximal end of radiating portion 12 to a distal end of cable 15 ranging between about 1 to 10 inches. Most feedlines may be constructed of copper, gold, or other conductive metals with similar conductivity values, but feedline 14 is preferably made of stainless steel. The metals may also be plated with other materials, e.g., other conductive materials, to improve their properties, e.g., to improve conductivity or decrease energy loss, etc. A feedline 14, such as one made of stainless steel, preferably has an impedance of about 50 Ω and to improve its conductivity, the stainless steel may be coated with a layer of a conductive material such as copper or gold. Although stainless steel may not offer the same conductivity as other metals, it does offer strength required to puncture tissue and/or skin.

FIGS. 2A and 2B show an end view and a cross-sectional view, respectively, of a conventional dipole microwave antenna assembly 30. As seen, antenna assembly 30 has a proximal end 32 which may be connected to a feedline 14, as further discussed herein, and terminates at distal end 34. The radiating portion of antenna 30 comprises proximal radiating portion 36 and distal radiating portion 38. Proximal radiating portion 36 may typically have an outer conductor 42 and an inner conductor 44, each of which extends along a longitudinal axis. Between the outer and inner conductors 42, 44 is typically a dielectric material 46 which is also disposed longitudinally between the conductors 42, 44 to electrically separate them. A dielectric material may constitute any number of appropriate materials, including air. Distal portion 48 is also made from a conductive material, as discussed below. Proximal and distal radiating portions 36, 38 align at junction 40, which is typically made of a dielectric material, e.g., adhesives, and are also supported by inner conductor 44 which runs through junction opening 50 and at least partially through distal portion 48. However, as discussed above, the construction of conventional antenna assembly 30 is structurally weak at junction 40.

In operation, microwave energy having a wavelength, $\lambda$, is transmitted through antenna assembly 30 along both proximal and distal radiating portions 36, 38. This energy is then radiated into the surrounding medium, e.g., tissue. The length of the antenna for efficient radiation may be dependent at least on the effective wavelength, $\lambda_{eff}$, which is dependent upon the dielectric properties of the medium being radiated into. Energy from the antenna assembly 30 radiates and the surrounding medium is subsequently heated. An antenna assembly 30 through which microwave energy is transmitted at a wavelength, $\lambda$, may have differing effective wavelengths, $\lambda_{eff}$, depending upon the surrounding medium, e.g., liver tissue, as opposed to, e.g., breast tissue. Also affecting the effective wavelength, $\lambda_{eff}$, are coatings which may be disposed over antenna assembly 30, as discussed further below.

FIG. 3 shows an exploded cross-sectional view of a variation on pre-stressed antenna assembly 60 made at least in part according to the present invention. In making antenna assembly 60, junction member 62 may be placed about inner conductor 44 through junction opening 64. Distal portion 48 may be placed over inner conductor 44 and then compressed such that junction member 62 is placed under a compressive load generated between proximal radiating portion 36 and distal radiating portion 38 to create pre-stressed antenna assembly 70, as shown in FIG. 4. Antenna assembly 70 may have an overall length of about 1.42 inches and an outer diameter of about 0.091 inches. The pre-stressed loading condition on antenna assembly 70 preferably exists when assembly 70 is under a state of zero external stress, that is, when assembly 70 is not acted upon by any external forces, e.g., contact with tissue, external bending moments, etc.

The compression load is preferably first created by feeding distal portion 48 over inner conductor 44 until junction member 62 is under compression, then inner conductor 44 is preferably affixed to distal portion 48 to maintain the compression load on junction member 62. Some clearance may be necessary between junction member 62 and inner conductor 44 to avoid any interference resistance between the two. Inner conductor 44 may be affixed to distal portion 48 along interface 72 by a variety of methods, such as welding, brazing, soldering, or by use of adhesives. The compression loading occurs such that while inner conductor 44 is placed under tension along direction 76, distal portion 48 places the outer portions of junction member 62 under compression along directions 74. Inner conductor 44 may be heated prior to affixing it to distal portion 48 by any number of methods because heating inner conductor 44 may expand the conductor in a longitudinal direction (depending upon the coefficient of thermal expansion of the inner conductor 44).

For example, heating inner conductor 44 may be accomplished during the welding or soldering procedure. Upon cooling, inner conductor 44 may contract accordingly and impart a tensile force upon the conductor 44 while simultaneously pulling junction member 62 into compression. To allow the compression loading to transfer efficiently through assembly 70, junction member 62 is preferably made of a dielectric material which has a sufficiently high compressive strength and high elastic modulus, i.e., resistant to elastic or plastic deformation under a compression load. Therefore, junction member 62 is preferably made from materials such as ceramics, e.g., $Al_2O_3$, Boron Nitride, stabilized Zirconia, etc. Alternatively, a junction member 62 made of a metal and sufficiently coated with a dielectric or polymer may be used, provided the dielectric coating is sufficiently thick to provide adequate insulation. To prevent energy from conducting directly into the tissue during use, a dielectric layer having a thickness between about 0.0001 to 0.003 inches, may be coated directly over antenna assembly 70. The dielectric coating may increase the radiated energy and is preferably made from a ceramic material, such as $Al_2O_3$, $TiO_2$, etc., and may also be optionally further coated with a lubricious material such as Teflon, polytetrafluoroethylene (PTFE), or fluorinated ethylene propylene (FEP), etc. In addition to the dielectric coating, a sealant layer may also be coated either directly over the antenna assembly 70, or preferably over the dielectric layer to provide a lubricious surface for facilitating insertion into a patient as well as to prevent tissue from sticking to the antenna assembly 70. The sealant layer may be any variety of polymer, but is preferably a thermoplastic polymer and may have a thickness varying from a few angstroms to as thick as necessary for the application at hand. Varying these coating thicknesses over antenna assembly 70 may vary the effective wavelengths, $\lambda_{eff}$, of the radiation being transmitted by the antenna. Thus, one may vary the coating thicknesses over the assembly 70 to achieve a predetermined effective wavelength depending upon the desired results.

Figure 5:
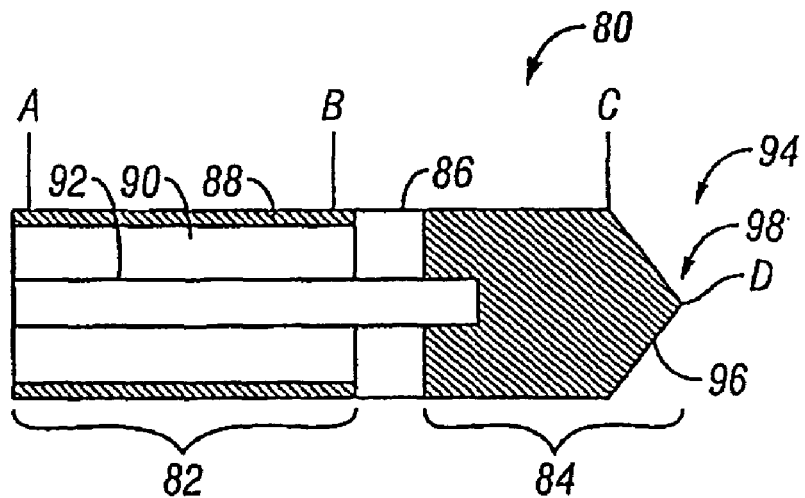
FIG. 5 shows another variation of pre-stressed antenna assembly having a sharpened distal tip.

FIG. 5 shows another variation of pre-stressed antenna assembly 80. This variation also has proximal radiating portion 82 attached to distal radiating portion 84 with junction member 86 therebetween under a compression load, as described above. Proximal radiating portion 82 may have outer conductor 88 and inner conductor 92 extending longitudinally with dielectric material 90 disposed in-between conductors 88, 92. However, this variation shows distal end 94 having distal radiating portion 84 with tapered end 96 terminating at tip 98, which is preferably sharpened to allow for easy insertion into tissue. A preferable method of optimizing the amount of radiated energy from assembly 80 may include adjusting the length of proximal radiating portion 82 to correspond to a length of $\lambda/4$ of the radiation being transmitted through assembly 80, and likewise adjusting a cumulative (or overall) length of distal radiating portion 84 and junction 86 to also correspond to a length of $\lambda/4$. Adjusting the lengths of proximal and distal radiating portions 82, 84 to correspond to the wavelength of the transmitted microwaves may be done to optimize the amount of radiated energy and accordingly, the amount of the medium or tissue which is subsequently heated. The actual lengths of proximal and distal radiating portions 82, 84 may, of course, vary and is not constrained to meet a $\lambda/4$ length. When antenna assembly 80 is radiating energy, the ablation field is variable 3-dimensionally and may be roughly spherical or ellipsoid and centers on junction 86 and extends to the ends of the proximal and distal radiating portions 82, 84, respectively.

The location of tip 98 may be proportional to a distance of λ/4 of the radiation being transmitted through assembly 80, but because tip 98 terminates at tapered end 96, the angled surface of taper 96 may be taken into account. Thus, the total distance along the outer surfaces of assembly 80 from B to C plus the distance from C to D may accord to the distance of λ/4. The length of proximal radiating portion 82, i.e., the distance along the outer surface of assembly 80 from A to B, may also accord to the distance of λ/4, as above. Although it is preferable to have the length of the radiating portion of the antenna accord with a distance of the wavelength, λ, it is not necessary for operation of the device, as described above. That is, an antenna assembly having a radiating portion with a length in accordance with a first wavelength may generally still be used for transmitting radiation having a second wavelength, or third wavelength, or so on, although with a possible reduction in efficiency.

Figure 6:
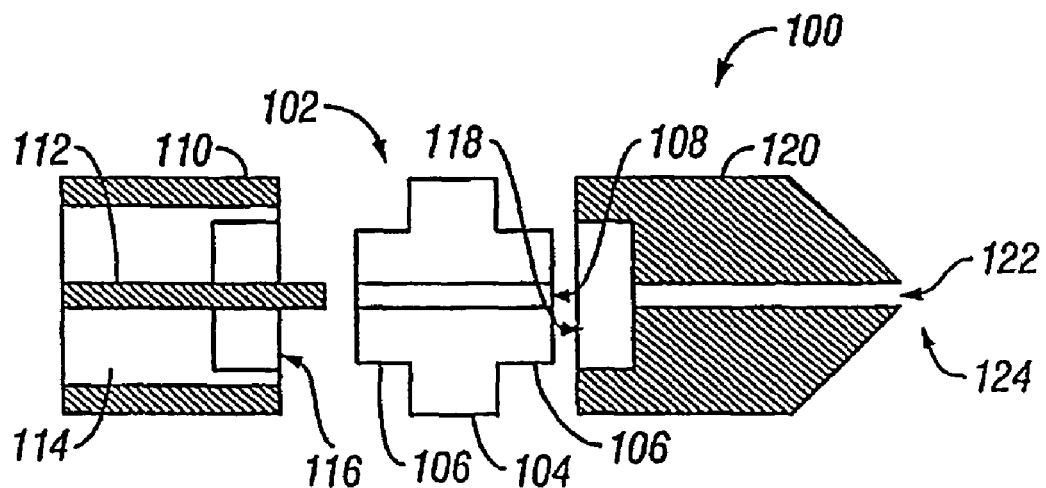
FIG. 6 shows an exploded cross-sectional view of another variation on pre-stressed antenna assembly having a non-uniform junction member.

FIG. 6 shows an exploded cross-sectional view of another variation on pre-stressed antenna assembly 100. Assembly 100 shows a variation of junction member 102 which has a radial thickness which is non-uniform about a longitudinal axis as defined by junction member 102. The proximal portion is comprised of outer conductor 110, inner conductor 112, dielectric material 114, as above. However, junction 102 is shown in this variation as a stepped member having at least two different radiuses. In other variations, the junction may be curved or have multiple steps. Central radius 104 of junction member 102 is shown as having a diameter similar to that of outer conductor 110 and distal portion 120. Stepped radius 106, which is preferably smaller than central radius 104, may be symmetrically disposed both proximally and distally of central radius 104. To accommodate stepped junction member 102 during the assembly of antenna 100, receiving cavity 116 may be made in dielectric material 114 and receiving cavity 118 may be made in distal portion 120 to allow for the interfitting of the respective parts. Such a stepped design may allow for the compression load to be concentrated longitudinally upon the central radius 104 of junction member 102 to allow for the efficient transfer of the load along the proximal portion.

In addition to stepped junction member 102, FIG. 6 also shows channel 122 extending longitudinally from distal tip 124 to receiving cavity 118. Once inner conductor 112 may be placed through junction opening 108 and into distal portion 120, either partially or entirely therethrough, channel 122 may allow for access to inner conductor 112 for the purpose of affixing it to distal portion 120. Affixing inner conductor 112 may be done to place it under tension by any of the methods as described above, such as welding or soldering.

Figure 7:
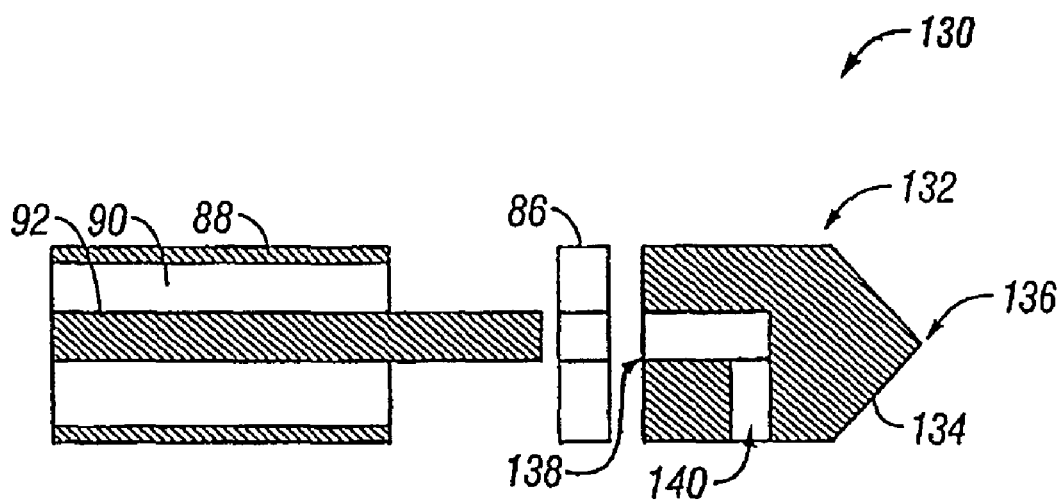
FIG. 7 shows an exploded cross-sectional view of yet another variation on pre-stressed antenna assembly having an access channel defined along the side of the antenna.

However, having channel 122 extend from the distal tip 124 to inner conductor 112 may limit the sharpness of tip 124. Accordingly, variation 130 in FIG. 7 shows an alternate distal end 132 which defines channel 138 for receiving inner conductor 92 but which also defines access channel 140 extending from a side surface of distal end 132 to channel 138. Access channel 140 allows for access to inner conductor 92 to affix it to distal end 132 while allowing for tapered end 134 to terminate at sharpened tip 136. Although a single channel is shown in this variation, multiple channels may be incorporated into the design at various locations.

Figure 8:
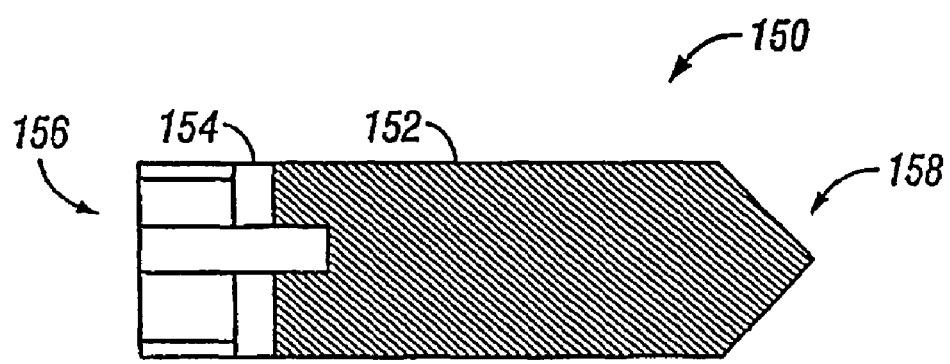
FIG. 8 shows a pre-stressed monopole variation of a microwave antenna assembly.

While most of the variations described above are related to dipole antenna assemblies, FIG. 8 shows monopole antenna assembly 150 made at least in part according to the present invention. As shown, there may be a single radiating portion 152 which preferably has a length corresponding to a length of λ/2, rather than λ/4, of the radiation being transmitted through assembly 150. As above, monopole assembly 150 may apply a compressive load upon junction member 154 between radiating portion 152 and proximal end 156. The principles of having an antenna length correspond to a length of λ/2 or λ/4, as well as having tapered distal ends or tips on the distal portion, may be utilized not only with antennas assembled using compression methods, but these principles may be used with any of the variations described herein.

To improve the energy focus of an antenna assembly, an electrical choke may also be used to contain returning currents to the distal end of the antenna. Generally, the choke may be disposed on the antenna proximally of the radiating section. The choke is preferably placed over a dielectric material which may be disposed over the antenna. The choke is preferably a conductive layer and may be further covered by a tubing or coating to force the conductive layer to conform to the underlying antenna, thereby forcing an electrical connection (or short) more distally and closer to the radiating section. The electrical connection between the choke and the underlying antenna may also be achieved by other connection methods such as soldering, welding, brazing, crimping, use of conductive adhesives, etc. The following description is directed towards the use of a choke on a compression antenna variation for illustration purposes only; however, the choke may also be used with any of the antenna variations described below.

FIG. 9A shows a side view of a variation on pre-stressed antenna assembly 160 with an electrical choke and FIG. 9B shows cross-sectioned side view 9B-9B from FIG. 9A. Similar to the antenna assemblies above, assembly 160 shows radiating portion 162 electrically attached via feedline (or shaft) 164 to a proximally located coupler 166. Detail 174 of radiating portion 162 and detail 180 of feedline 164 are described in further detail below. Radiating portion 162 is shown with sealant layer 168 coated over section 162. Electrical choke 172 is shown partially disposed over a distal section of feedline 164 to form electrical choke portion 170, which is preferably located proximally of radiating portion 162. Details 176, 178 of choke portion 170 are described in further detail below.

Figure 10:
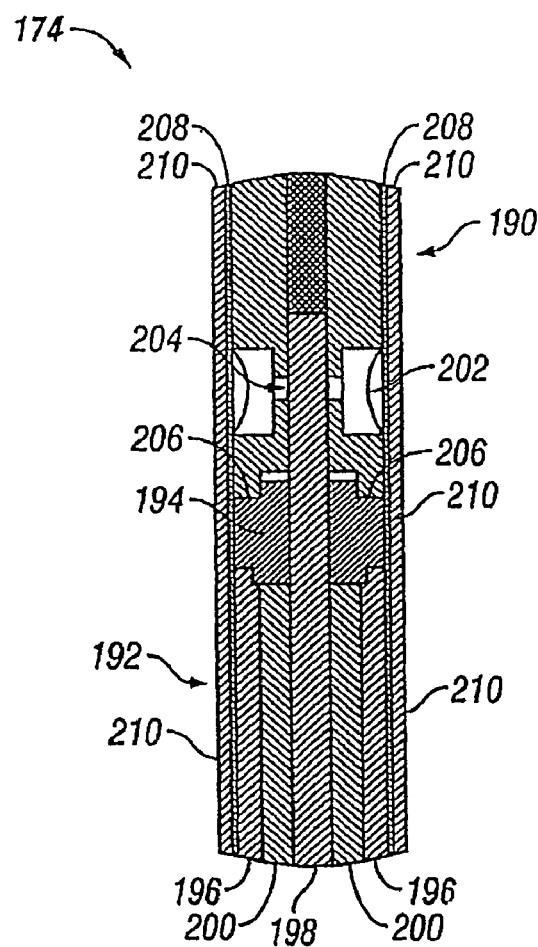
FIG. 10 shows a detailed view of a variation on the radiating portion of FIG. 9B.

FIG. 10 shows detailed view 174 from FIG. 9B of a variation on a pre-stressed antenna section. As seen, distal radiating portion 190 and proximal radiating portion 192 are located in their respective positions about junction member 194, which in this variation is shown as a stepped member. Proximal radiating portion 192 is further shown having outer conductor 196 preferably disposed concentrically about inner conductor 198 with dielectric 200 placed inbetween outer and inner conductors 196, 198 for insulation. Inner conductor 198 may be fed through junction member 194 and into distal radiating portion 190 to be affixed by weld or solder 202 to distal radiating portion 190 via access channel 204, which is shown to extend from a distal end of inner conductor 198 to an outer surface of portion 190. As described above, inner conductor 198 may be heated to longitudinally expand it prior to affixing it to distal portion 190. As inner conductor 198 cools, a tensile force is imparted in inner conductor 198 which draws the distal and proximal portions 190, 192 together longitudinally. In turn, this imparts a compressive force upon the radial portions of junction member 194, preferably at the junction-to-distal portion interface 206. Optionally, dielectric layer 208, which may be a ceramic material such as $Al_2O_3$, may be coated over the radiating antenna portion. Moreover, a lubricious layer such as Teflon, may also be coated over the antenna portion as well along with dielectric layer 208. A further sealant layer 210 may optionally be coated over dielectric layer 208 as well. Sealant layer 210 may be made from a variety of thermoplastic polymers, e.g., heat shrink polymers, such as polyethylene (PE), polyethylene terephthalate (PET), polytetrafluoroethylene (PTFE), fluorinated ethylene propylene (FEP), perfluoroalkoxy (PFA), chlorotrifluoroethylene (CTFE), ethylene chlortrifluoroethylene (ECTFE), and ethylene tetrafluoroethylene (ETFE). The description is directed towards the use of dielectric and sealant layers on a compression antenna variation for illustration purposes only; however, the uses of dielectric and sealant layers may also be used with any of the antenna variations described below.

Figure 11:
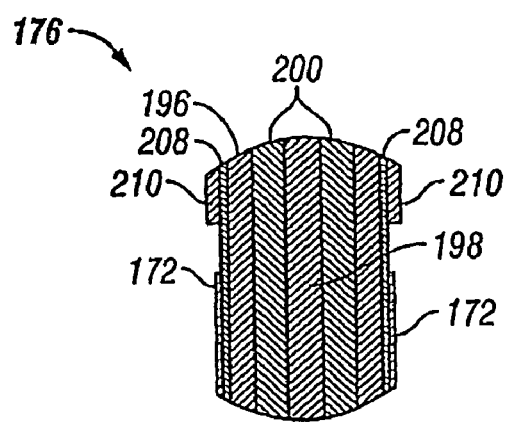
FIG. 11 shows a detailed view of a variation on the transition from the radiating portion to the electrical choke of FIG. 9B.
Figure 12:
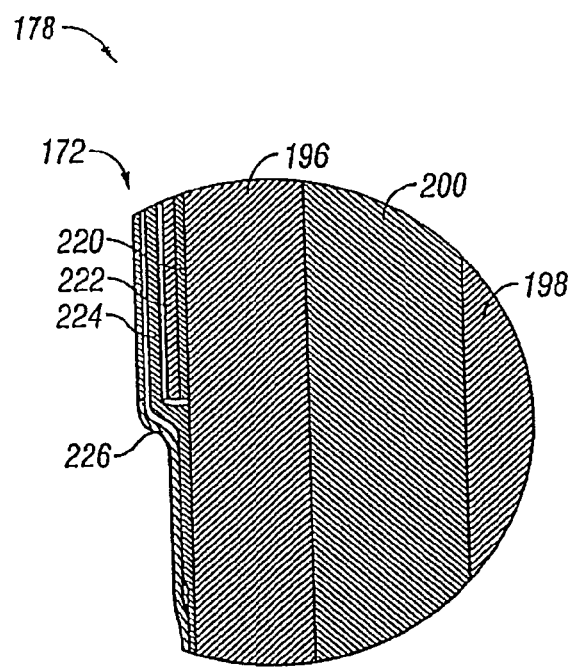
FIG. 12 shows a detailed view of a variation on the different layers within the electrical choke of FIG. 9B.

FIG. 11 shows detailed view 176 from FIG. 9B of a variation on the transition to electrical choke portion 170. Electrical choke 172 may be disposed proximally of sealant layer 210 or proximal radiating portion 192. Although shown with a gap between choke 172 and sealant layer 210 in this variation, the two may touch or overlap slightly. FIG. 12 shows a more detailed view 178 of the various layers which may comprise electrical choke 172. In this variation, a first inner dielectric layer 220 may be disposed over the antenna assembly. The first inner dielectric layer 220 may be made from any of the various thermoplastic polymers, ceramics, or other coatings, as described above. A second inner dielectric layer 222 may optionally be disposed over first inner dielectric layer 220 and may be made from the same or similar material as first inner dielectric layer 220. Conductive layer 224 may then be disposed over the dielectric layers. Conductive layer 224 is preferably a conductive coating, a conductive foil material, e.g., copper foil, or a metal tubing and electrically contacts outer conductor 196 at some location along choke 172 proximally of radiating portion 162.

Figure 13:
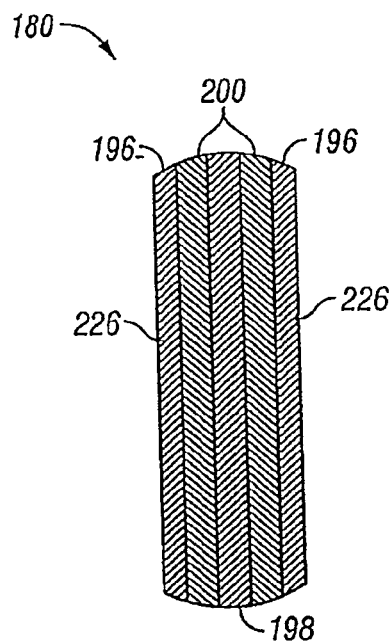
FIG. 13 shows a detailed view of a variation on the feedline of FIG. 9B.

Variation 160 illustrates electrical contact between conductive layer 224 and outer conductor 196 in detail 178 occurring at the proximal location of electrical choke portion 170, but choke 172 may be formed without forcing contact between outer conductor 196 with layer 224 provided the length of choke 172 is chosen appropriately. For instance, choke 172 having a sufficiently long length, e.g., a length of λ/2, may be used without having to force contact between the layers. Outer dielectric layer 226 may be disposed upon conductive layer 224. Outer dielectric layer 226 may also be made of any of the various polymers as described above and is preferably a heat shrinkable layer that may force conductive layer 224 to conform more closely to the underlying layers to not only force a better electrical connection, but also to reduce the overall diameter of the antenna section. FIG. 13 shows detailed view 180 from FIG. 9B of a variation on the feedline. As shown, feedline 164 may be a simple coaxial cable where outer conductor 196, inner conductor 198, and dielectric 200 extend throughout the feedline. Outer dielectric layer 226 may also extend down over feedline 164 and even over the entire antenna assembly.

Figure 14:
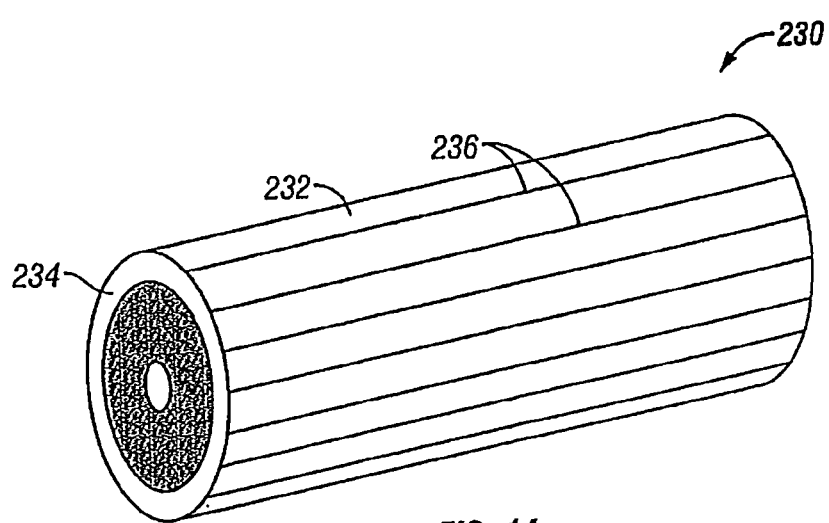
FIG. 14 shows an isometric view of a sectioned antenna assembly having a layer, such as a heatshrink layer, formed with wires or strands longitudinally orientated within the layer.

Further steps may optionally be taken to further increase the strength of an antenna assembly by altering any of the layers, such as sealant layer 210 or any of the other heatshrink layers discussed above. FIG. 14 shows one example of antenna section 230 where wires or strands 236 may be formed within or on the layers 232 to add strength. The wires 236 may be formed within the layer 232 and are preferably orientated longitudinally along the length of antenna section 230 such that the bending strength of the antenna is increased. The layers 232 may be formed over outer conductor 234, as described above, and wire 236 may be made of any high-strength material, e.g., Kevlar, metals, etc. Metal wires may be used provided they are well insulated by layers 232.

Antenna Assembly Via Mechanical Fastening

Figure 15:
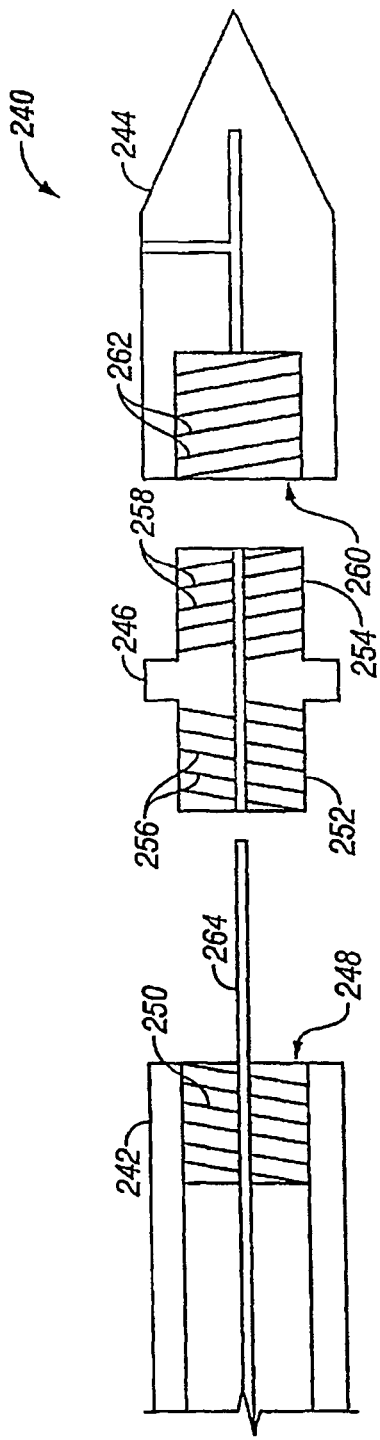
FIG. 15 shows an exploded cross-sectional side view of a variation of the microwave antenna assembly having a mechanically threaded interface.

Aside from using a compressive load to increase antenna strength, as described above, alternative methods may be employed for increasing antenna strength to withstand direct insertion into tissue. An alternative variation may include assembling an antenna using mechanical fastening methods. FIG. 15, for example, shows a cross-sectioned variation of a mechanically threaded interface or "screw-on" variation 240 as an exploded assembly. As seen, proximal portion 242 may be connected to distal portion 244 by using a junction member 246 having first and second junction mating sections 252, 254, respectively.

Junction member 246 is preferably comprised of any of the dielectric materials as described above. Alternatively, a dielectric coating or layer may also be applied to the inside of channels 248, 260 which contacts junction member 246. First and second mating sections 252, 254 may be threaded 256, 258, respectively, such that the thread pitch on each section 252, 254 is opposed to each other, i.e., the pitch angle of threading 256 may be opposite to the pitch angle of threading 258. Alternatively, the thread pitch on each section 252, 254 may be configured to be angled similarly for ease of antenna assembly. Proximal portion 242 may have a receiving cavity or channel 248 which is threaded 250 at a predetermined pitch to correspond to the pitch and angle of the threading 256 on first mating section 252. Likewise, distal portion 244 may have a receiving cavity or channel 260 which is threaded 262 at a predetermined pitch to correspond to the pitch and angle of the threading 258 on second mating section 254. Having opposed pitch angles may be done to ensure a secure fit or joint when variation 240 is assembled by screwing proximal portion 242 and distal portion 244 together onto junction member 246.

Figure 16:
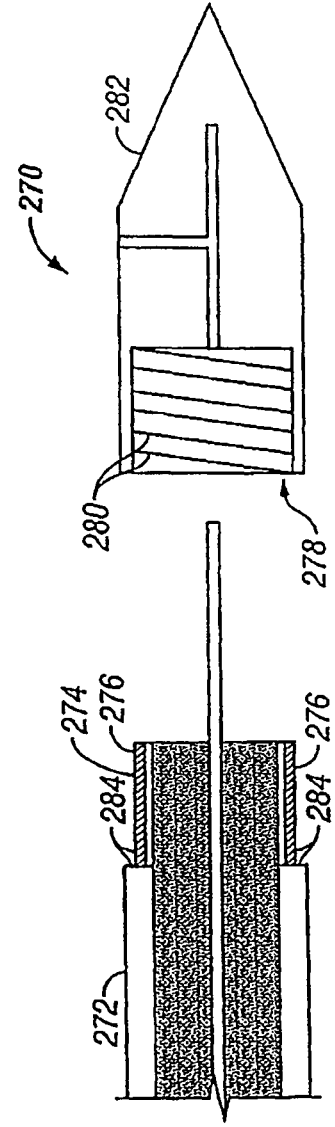
FIG. 16 shows an exploded cross-sectional side view of another variation of the antenna assembly also having a mechanically threaded interface.

A further screw-on variation 270 is shown in FIG. 16. Here, proximal portion 272 may have a proximal mating section 274 which is threaded 276 at a predetermined pitch and angle to correspondingly screw into distal portion 282 via threaded receiving channel 278. Channel 278 preferably has threading 280 which matches threading 276 on mating section 274 to ensure a tight fit and a secure joint. Although variation 270 shows a mating section 274 on proximal portion 272 and receiving channel 278 in distal portion 282, a mating section may instead be located on distal portion 282 for insertion into a corresponding receiving channel located in proximal portion 272. Preferably, a dielectric coating or layer 284 is applied either to the inside of channel 278 or on the outer surface of mating section 274 as shown (or upon both) to prevent contact between proximal and distal portions 272, 282, respectively.

Antenna Assembly Via Overlap

Figure 17:
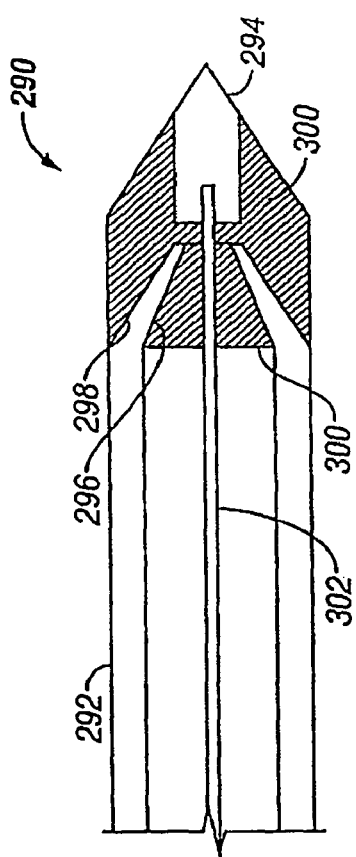
FIG. 17 shows a cross-sectional side view of a crimped or overlapping variation of the antenna assembly.

Another variation on assembling an antenna is by use of overlapping or interfitting joints to attach proximal and distal portions together. FIG. 17 shows a crimped or overlapping variation 290. Proximal portion 292 is preferably attached to distal tip or portion 294 by inner conductor 302 and by having a distal end section of the proximal portion 292 crimped and portion 294 maintained in position via a molded material 300, which is also preferably dielectric such as a biocompatible thermoset plastic or polymer (including any of the dielectric materials discussed herein). The distal end section, i.e., crimped dielectric 296 and crimped outer conductor 298, is preferably crimped or tapered in a reduced diameter towards the distal end while a portion of dielectric 296 near crimped outer conductor 298 may be partially removed to allow for material 300 to be formed within, as shown in the figure. While the inner conductor 302 is held between proximal and distal portions 292, 294, respectively, the moldable material 300 may be injection molded within a die or preform holding the assembly to form a unitary structure with both portions 292, 294. Material 300 may also be shaped into various forms depending upon the desired application, such as a tapering distal end, as shown in the FIG. 17.

Figure 18:
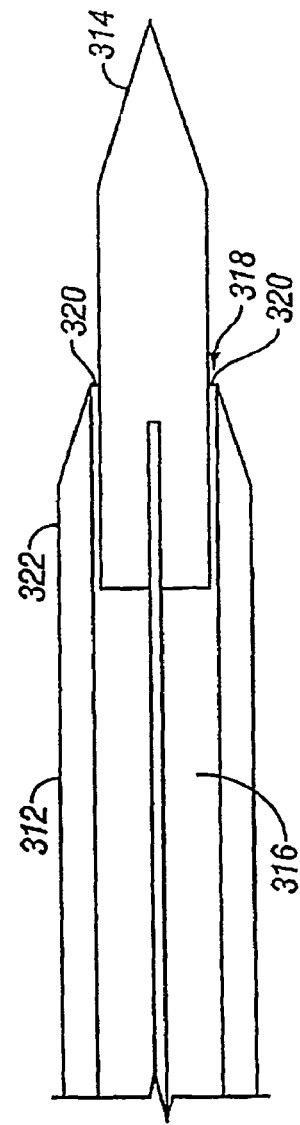
FIG. 18 shows a cross-sectional side view of an antenna assembly where the proximal portion may be configured to receive and hold the distal portion in an overlapping joint.

FIG. 18 shows another variation 310 where proximal portion 312 is preferably configured to receive and hold distal portion 314. Proximal portion 312 may have a distal section of dielectric material 316 removed partially to create a receiving channel 318 within portion 312. Distal portion 314 may be snugly placed within this channel 318 such that portion 314 is partially within and partially out of dielectric material 316, as shown. A layer 320 of the dielectric material 316 may be left between outer conductor 322 and distal portion 314 to form an insulative barrier between the two. Alternatively, dielectric layer 320 may be formed of a different material than dielectric 316. To further aid in antenna 310 insertion into tissue, the distal end of distal portion 314, as well as the distal end of outer conductor 322, may be tapered to facilitate insertion. The overlapping segment between proximal and distal portions 312, 314, respectively, may be varied depending upon the desired bending resistance and desired strength of antenna 310.

Figure 19:
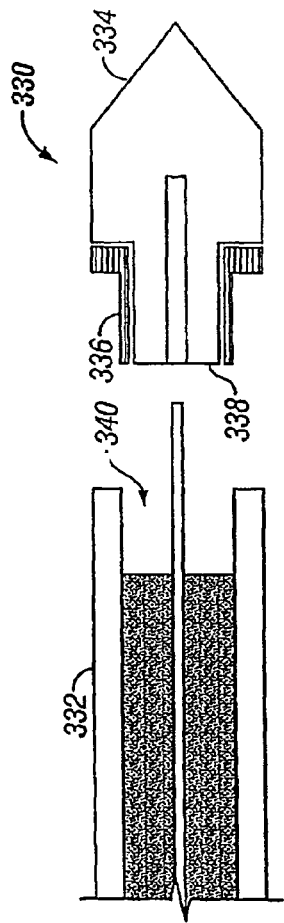
FIG. 19 shows an exploded cross-sectional side view of a variation of the antenna assembly having an interfitting joint with an overlapping junction member.

FIG. 19 shows a further variation 330 of an overlapping joint for assembling the antenna. Proximal portion 332 preferably has a mating channel 340 in the distal end of the portion 332 for receiving mating section 338 of distal portion 334. This variation 330 preferably has an overlapping junction member 336 which may be slipped over mating section 338 prior to insertion into channel 340. Overlapping junction member 336 is preferably a dielectric material and fits snugly between proximal portion 332 and mating section 338 to form an overlapping joint when the inner conductor is attached to distal portion 334, as described above.

Figure 20:
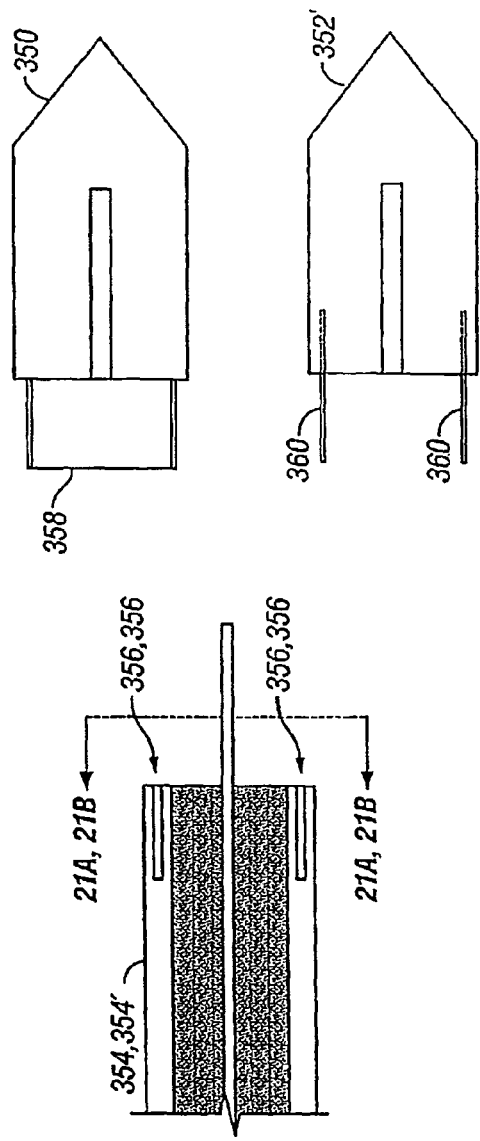
FIG. 20 shows a cross-sectional side view of an antenna assembly with two variations on the distal portion joint for interfitting with the proximal portion.
Figure 21A:
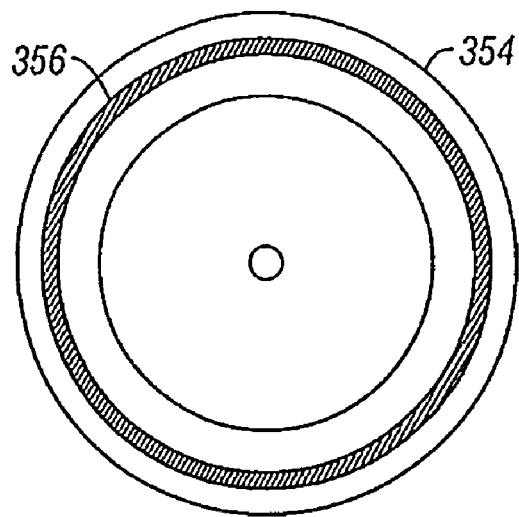
FIGS. 21A and 21B show the corresponding end views of the proximal portion from FIG. 20 with two variations for interfitting with the distal portions.

FIG. 20 shows an antenna variation where different methods of overlapping attachments may be utilized. Distal portion 350 is shown having a cylindrical interfitting member 358. The portion 350 may be inserted via member 358 into a corresponding receiving channel 356 preferably defined in the outer conductor of proximal portion 354. An end view of proximal portion 354 in FIG. 21A shows channel 356 in this variation for receiving a cylindrically shaped member 358.

Figure 21B:
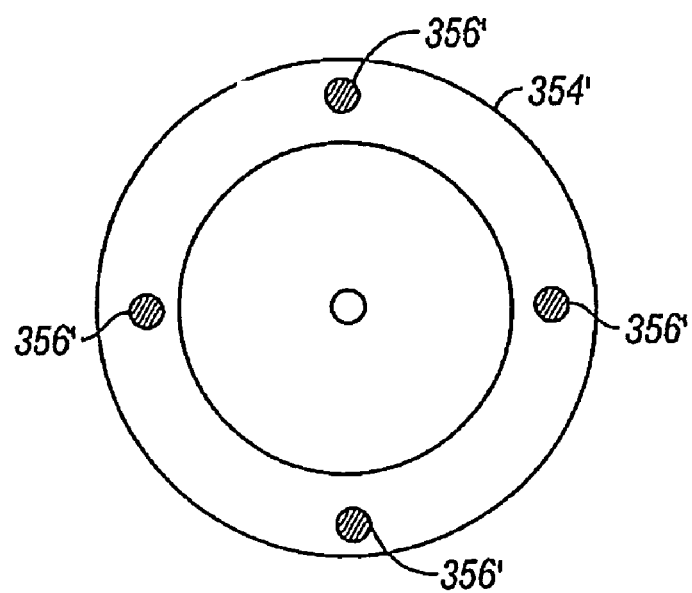

Another variation is shown in distal portion 352 where rather than having a conical interfitting member, separate pins or dowels 360 may be used to extend into receiving channels 356' of proximal portion 354'. These pins 360 may be integral with distal portion 352 or they may be separate members inserted and held in distal portion 352; in either case, pins 360 are preferably made of a hard dielectric material or a metal sufficiently coated with a dielectric material for insulation. As seen in FIG. 21B, which is an end view of proximal portion 354', channels 356' are shown located every 90° about portion 354'. Although four pins are used in this variation, any number of pins may be used ranging from two to several depending upon the desired strength of the antenna assembly. To support such a plurality of pins, it may be desirable to have proximal portions 354, 354' with an outer conductor having a thickness ranging from 0.005 to 0.010 inches.

FIG. 22 shows an antenna assembly with an overlapping interference-fitted variation 370. As seen, proximal portion 372 may be attached to distal portion 374 by a junction member 376 which is preferably interference-fitted, i.e., frictionally-fitted, between both portions 372, 374. The junction member 376 may have a first and a second section 382, 384, respectively, which preferably has a diameter $D_2$. Receiving channel 378 in proximal portion 372 preferably has a diameter $D_1$ and receiving channel 380 in distal portion 374 also has a diameter $D_1$ or some diameter less than $D_2$. Accordingly, diameter $D_1$ is some value less than $D_2$ such that an interference fit is created between junction 376 and portions 372 and 374. Accordingly, distal portion 374 is frictionally held to proximal portion 372.

FIG. 23 shows another interfitting variation 390 utilizing a junction member 396 which is preferably held between proximal portion 392 and distal portion 394 by multiple pins 398, 402 which may be received in channels 400, 404, respectively. Accordingly, as discussed above, any number of pins 398 extending from proximal portion 392 may be inserted into corresponding channels 400, and any number of pins 402 extending from distal portion 394 may likewise be inserted into corresponding channels 404.

Figure 24:
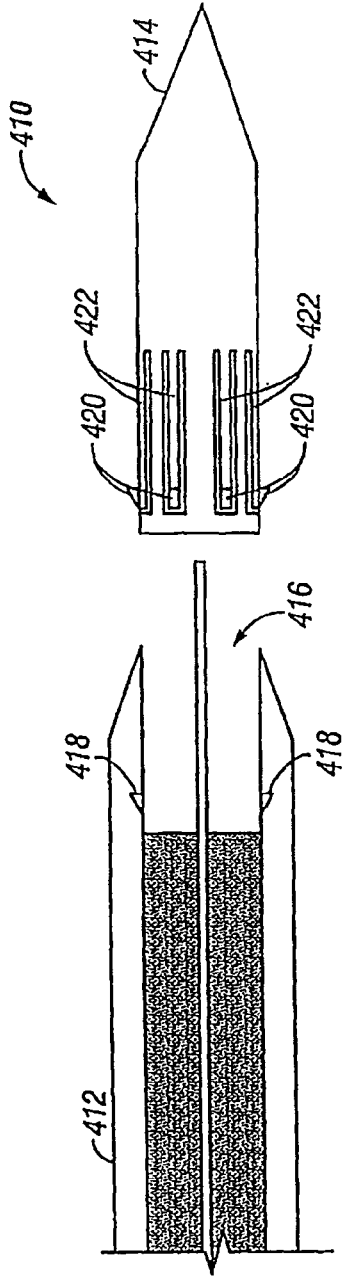
FIG. 24 shows an exploded cross-sectional side view of another variation in which the distal portion may have a plurality of projections which interfit with corresponding depressions within the proximal portion.

FIG. 24 shows an overlapping and interfitting variation 410 where proximal portion 412 has receiving channel 416 for receiving distal portion 414. Within channel 416, there may be a plurality of depressions 418 defined in the surface of the outer conductor. These depressions 418 are preferably shaped to have a locking configuration, such as a right triangle shape, when projections 420, which are located radially on distal portion 414, are inserted into and mated to depressions 418. Projections 420 are preferably protrusions which extend from a surface of distal portion 414 and are preferably radially disposed on the outer surface. Also, any number of projections 420, e.g., at least two to several, may be utilized but are preferably equally radially spaced from one another depending upon the desired strength of the overlapping joint. To facilitate insertion of distal portion 414 into channel 416, projections 420 may be disposed on the ends of a number of corresponding support members 422 flexibly attached to distal portion 414. Support members 422 would allow projections 420 to be retracted at least partially into the outer surface of distal portion 414 during insertion, and when distal portion 414 is fully inserted into channel 416, projections 420 may then be allowed to expand into and intimately mate with the depressions 418 such that distal portion 414 is held fixed relative to proximal portion 412. A dielectric material may be coated or sprayed within channel 416 or on distal portion 414 to insulate between the two portions 412, 414.

Figure 25:
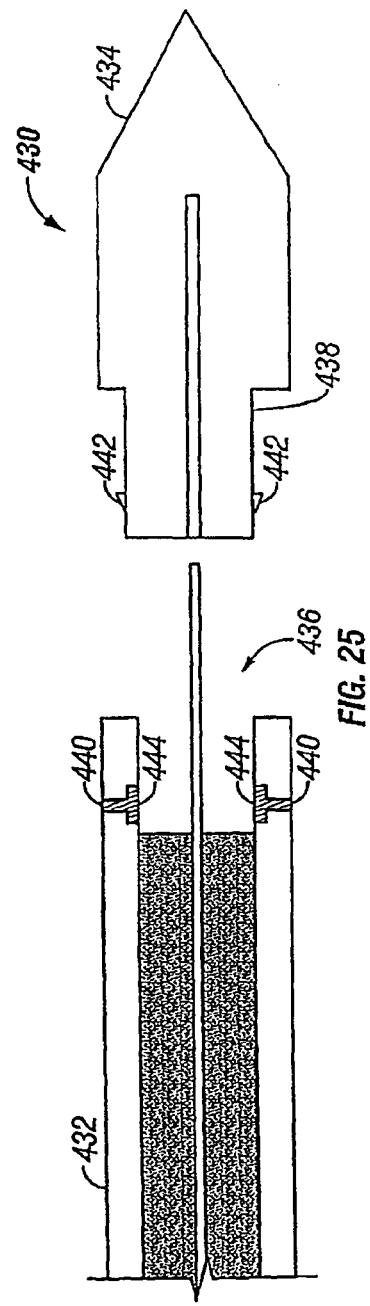
FIG. 25 shows another variation in which the projections and their corresponding interfitting depressions may have corresponding access channels defined in the proximal portion through which the distal portion may be welded, soldered, brazed, or adhesively affixed to the proximal portion.

FIG. 25 shows a further variation 430 of that shown in FIG. 24. Proximal portion 432 may be attached to distal portion 434 by an overlapping joint where mating section 438 on distal portion 434 may be inserted into receiving channel 436. Once inserted, distal portion 434 may be held to proximal portion 432 by projections 442 intimately mating within corresponding depressions 444. Distal portion 434 may be made entirely of a dielectric material; alternatively, mating section 438 may be made at least partly of a dielectric while the remainder of distal portion 434 may be metallic. To further ensure a strong joint, depressions 444 may have a number of access channels 440 preferably extending radially from depressions 444 defined in the surface of channel 436 to an outer surface of proximal portion 432. Access channels 440 may be used to provide access to projections 442 (once mated within depressions 444) for further fixation to proximal portion 432 by welding, soldering, brazing, or by applying adhesives.

Alternate Methods of Tip or Distal Portion Attachment

Aside from various methods of assembling microwave antennas, there are also a variety of methods for attaching the tip or distal radiating portion to a remainder of the assembly. The various methods described below may be used in any of the assembly variations discussed herein depending upon the desired antenna assembly characteristics.

Figure 26:
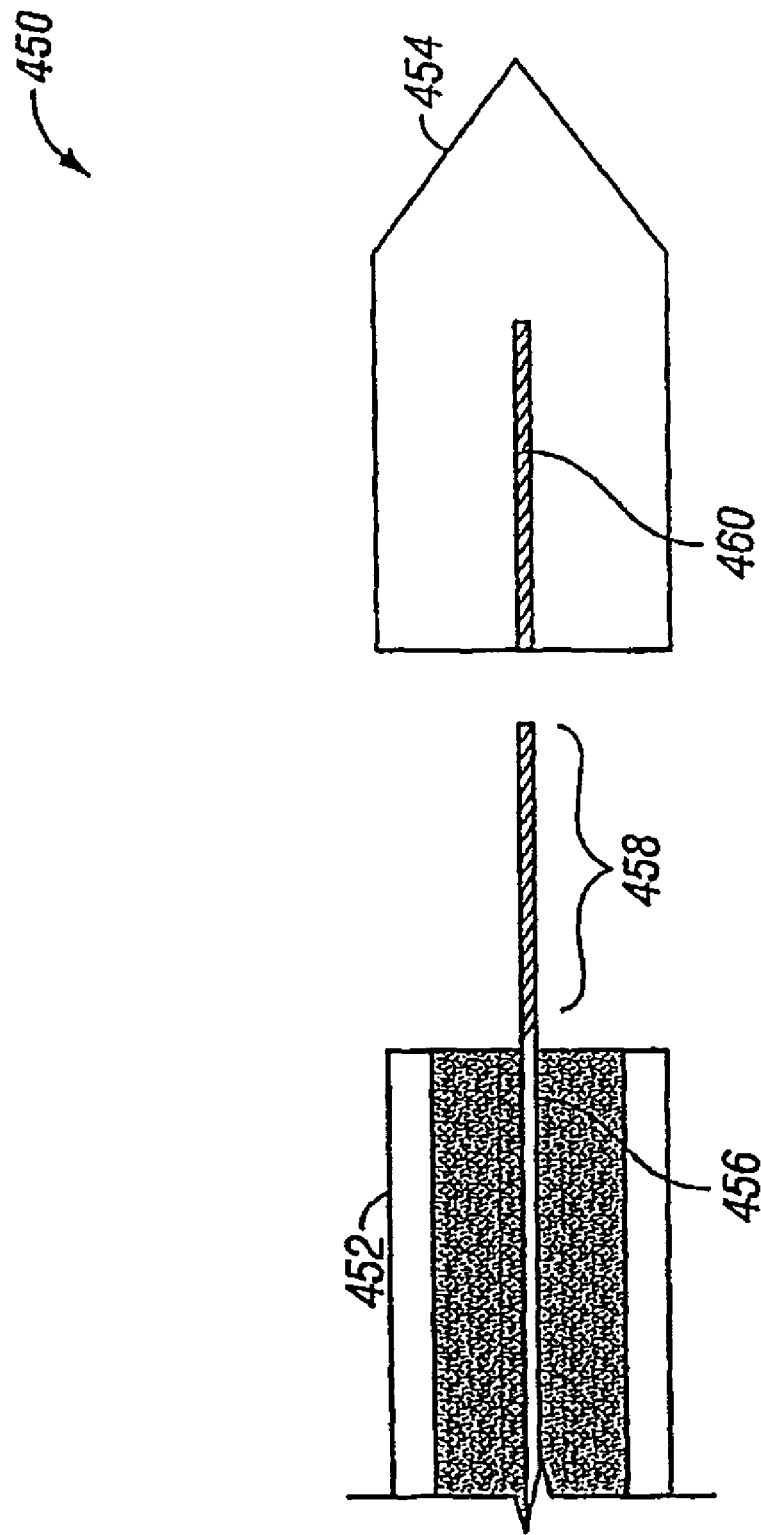
FIG. 26 shows a side view of a variation on attaching the distal portion to the inner conductor by a screw-on method.

FIG. 26 shows a partial assembly of a microwave antenna having a distal portion 454 which may be screwed onto the proximal portion 452 via the inner conductor 456. The distal end portion of inner conductor 456 is preferably threaded 458 on an outer surface. Correspondingly, the receiving channel 460 within distal portion 454 is likewise threaded to receive the threaded portion 458 of inner conductor 456. During assembly, distal portion 454 may be screwed onto proximal portion 452 by inner conductor 458. Accordingly, the force with which the proximal and distal portions 452, 454 are held together may be varied by the amount and degree distal portion 454 is screwed or advanced onto inner conductor 456, thereby allowing the rigidity or strength of the antenna to be varied according to a desired use or application. In this variation, distal portion 454 may be made of a non-metallic material, e.g., a polymer, and attached directly to proximal portion 452; alternatively, distal portion 454 may also be made of a metallic material and used in conjunction with a dielectric junction member, as described above.

FIG. 27 shows another variation for assembling a distal portion in an isometric exploded view of splittable distal portion 470. The distal portion 470 may be comprised of a splittable distal portion having a first half 472 and a second half 474. Although shown split into two halves 472, 474, distal portion 470 may be split into numerous portions, e.g., three or more. Within the adjoining surfaces, anchoring channel 476 may be defined to receive inner conductor 480 and may have a portion of channel 476 configured or enlarged to receive an anchoring element 482 for holding the inner conductor 480 distal end within distal portion 470. Inner conductor 480 preferably has an anchoring element 482 formed on a distal end of inner conductor 480 by rounding or flattening the distal end into anchoring element 482 or attaching a separate anchoring mechanism onto the distal end. Once inner conductor 480 and anchoring element 482 are positioned within anchoring channel 476, both halves 472, 474 may be attached together, thereby fixedly holding anchoring element 482 therewithin. When distal portion halves 472, 474 are attached to one another, they may be aligned and positioned relative to each other by a number of alignment projections 478 on one or both halves 472, 474 and the halves may then be held to one another by any number of methods, e.g., welding, brazing, soldering, adhesives, snap-fits, etc.

Figure 28:
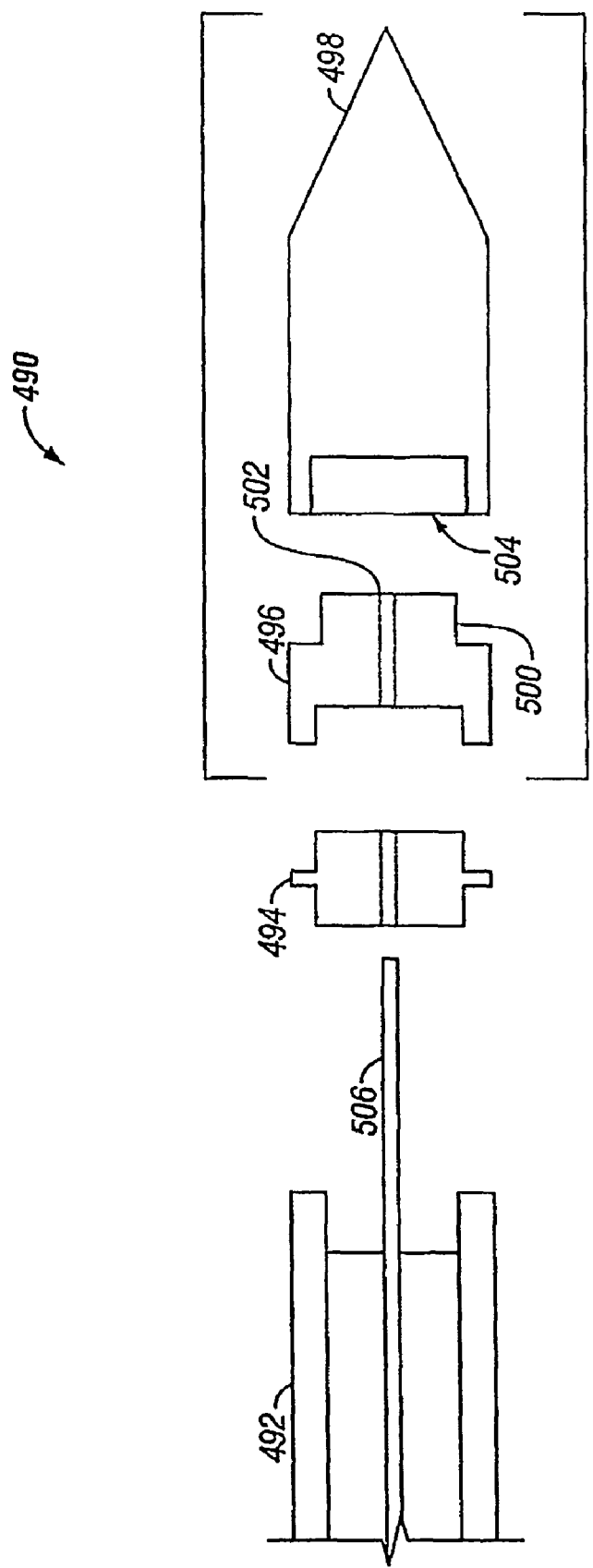
FIG. 28 shows an exploded side view of a multi-sectioned distal portion variation.

Another variation for attaching the distal portion is shown in FIG. 28, which is an exploded side view of multi-sectioned portion 490. The distal portion may be comprised of multiple sections which may be interfitted to form the distal portion. Thus, while proximal portion 492 and junction member 494 (which may or may not be used in this variation) are assembled as in some of the other variations, the distal portion may have a first section 496 through which inner conductor 506 may be passed through via access channel 502. Once the distal tip of inner conductor 506 is passed through junction member 494 and access channel 502, it may then be attached to first section 496 at the end of access channel 502 by any of the attachment methods described above. First section 496 may then be assembled with second section 498 by interfitting mating section 500 into receiving channel 504. The use of a multi-sectioned portion such as that shown in portion 490 may enable one to first attach the proximal portion with the distal portion and variably alter the tip of the distal portion according to a desired application.

To further aid in tip or distal portion attachment to the antenna assembly, various distal portions may be used to facilitate assembly and use in a patient. As previously described, the distal tip is preferably tapered and terminates at a tip to facilitate antenna insertion into tissue with minimal resistance. Also, attaching the inner conductor to the distal portion may be facilitated by an access channel defined in the distal portion so that the inner conductor may be attached by welding, soldering, etc. within the distal portion. To further facilitate this assembly process, the distal tip may be formed into an arcuate or curved face terminating into a tip, as seen in FIG. 29. As shown in the cross-sectional side view of alternate tip 510, it may have the arcuate or curved face 512 sloping distally such that tip 514 is formed off-center from the longitudinal axis defined by the antenna to which alternate tip 510 may be attached. Accordingly, inner conductor 518 may be routed through access channel 516 and then attached by any of the methods described to alternate tip 510 thereby allowing tip 514 to be sharpened as necessary and allowing an access channel 516 to be maintained along the longitudinal axis of the antenna for ease of assembly.

Alternate Distal Portion Attachments

As discussed above, the energy with a wavelength, $\lambda$, is transmitted down a microwave antenna and is subsequently radiated into the surrounding medium. In operation, microwave energy having a wavelength, $\lambda$, is transmitted through the antenna assembly along both proximal and distal radiating portions. This energy is then radiated into the surrounding medium. The length of the antenna for efficient radiation may be dependent at least on the effective wavelength, $\lambda_{\mathit{eff}}$, which is dependent upon the dielectric properties of the medium being radiated into. Energy having the effective wavelength radiates and the surrounding medium is subsequently heated. An antenna assembly through which microwave energy is transmitted at a wavelength, $\lambda$, may have differing effective wavelengths, $\lambda_{\mathit{eff}}$, depending upon whether the energy is radiated into, e.g., liver tissue, as opposed to, e.g., breast tissue. Also affecting the effective wavelength, $\lambda_{\mathit{eff}}$, are coatings which may be disposed over the antenna assembly.

Figure 30:
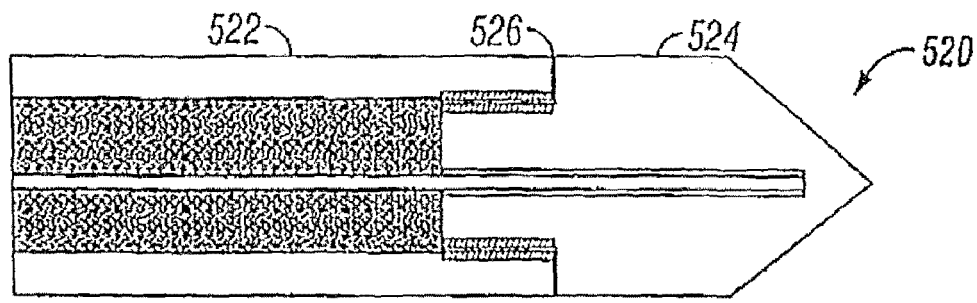
FIG. 30 shows an assembled cross-sectional side view of a representative antenna assembly having a constant diameter over the proximal and distal portions.
Figure 31:
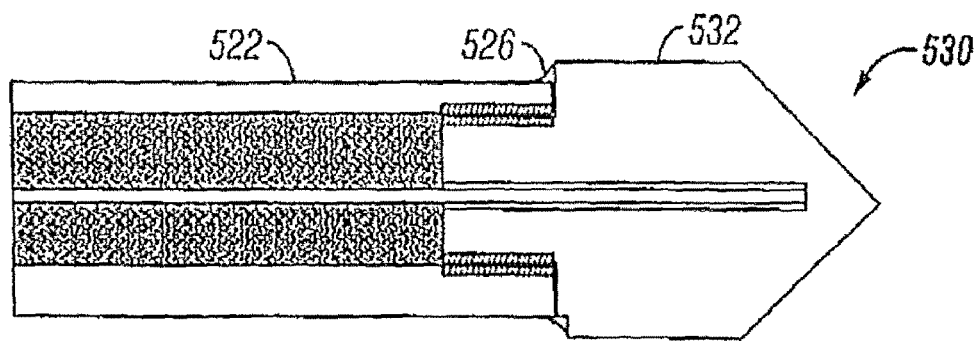
FIG. 31 shows the antenna of FIG. 30 but with the distal portion having a diameter larger than the diameter of the proximal portion.
Figure 32:
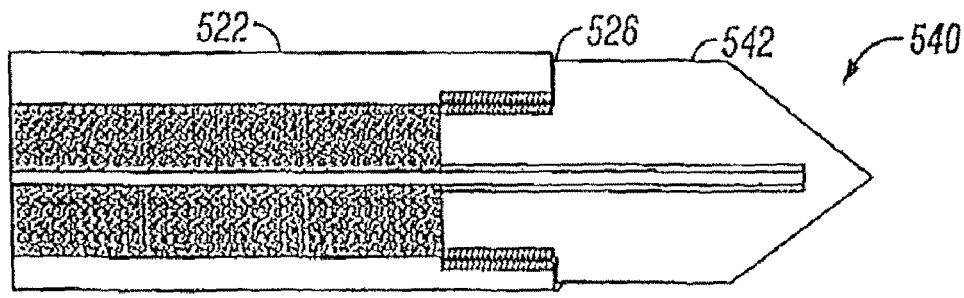
FIG. 32 shows the antenna of FIG. 30 but with the distal portion having a diameter smaller than the diameter of the proximal portion.

Accordingly, various distal portions having varying diameters are shown in FIGS. 30 to 32. FIG. 30, for instance, shows a representative antenna 520 having a constant diameter from proximal portion 522 to distal portion 524 while covered with an optional heatshrink 526, as described above, for comparison purposes. FIG. 31 shows antenna 530 having distal portion 532 with a larger diameter than proximal portion 522. Heatshrink 526 in this variation may be desirable to smooth the transition between the different diameters. On the other hand, FIG. 32 shows antenna 540 having distal portion 542 with a diameter that is smaller than that of proximal portion 522. Having heatshrink 526 in this variation may also be desirable to likewise smooth the transition between the different diameters. Varying the diameters of the distal portion may change the radiative properties of the effective wavelength in addition to the different medium types being radiated into. Accordingly, the diameter of the distal portion may be varied to give a desired radiative effect for different tissue types. Besides the diameter of the distal portion, the thicknesses of heatshrink 526 or any of the other dielectric and sealant layers, as described above, may also be varied accordingly in addition to the distal portion diameter. Although only two variations are shown in FIGS. 31 and 32, the distal tips may have a variety of configurations; for instance, it may be stepped, ramped, tapered, etc., depending upon the desired radiative effects.

The applications of the antenna assemblies and methods of making the assemblies discussed above are not limited to microwave antennas used for hyperthermic, ablation, and coagulation treatments but may include any number of further microwave antenna applications. Modification of the above-described assemblies and methods for carrying out the invention, and variations of aspects of the invention that are obvious to those of skill in the art are intended to be within the scope of the claims.

We claim:

1. A microwave antenna assembly for applying microwave energy therapy, comprising:
- a proximal radiating portion having an inner conductor and an outer conductor, each extending therethrough, the inner conductor disposed within the outer conductor;
- a distal radiating portion disposed distally of the proximal radiating portion, with the inner conductor extending at least partially therein;
- an electrical choke portion disposed proximally of the distal radiating portion and at least partially over the proximal radiating portion, the electrical choke portion having a conductive layer and at least one dielectric layer disposed between the conductive layer and the outer conductor of the proximal radiating portion; and
- a junction member having a longitudinal thickness and having at least a portion of which is disposed between the proximal and distal radiating portions such that the inner conductor extends therethrough,
- wherein the distal radiating portion and proximal portion apply a compressive force on at least a portion of the junction member.

2. A microwave antenna assembly according to claim 1, wherein the distal radiating portion defines a channel extending from the inner conductor disposed within the distal radiating portion to an outer surface of the distal radiating portion.

3. A microwave antenna assembly according to claim 1, wherein the distal radiating portion is attached to the inner conductor by a method selected from the group consisting of welding, brazing, soldering, and adhesives.

4. A microwave antenna assembly according to claim 1, wherein the electrical choke portion includes a pair of dielectric layers disposed between the conductive layer and the outer conductor.

5. A microwave antenna assembly according to claim 1, further comprising a sealant coating disposed at least partially over the distal radiating portion.

6. A microwave antenna assembly according to claim 5, wherein a gap is defined between the electrical choke portion and the sealant coating.

7. A microwave antenna assembly according to claim 5, wherein the electrical choke portion and sealant coating at least partially overlap.

8. A microwave antenna assembly according to claim 5, wherein the sealant coating comprises a thermoplastic polymer.

* * * * *